United States Patent [19]

Hübele

[11] Patent Number: 5,045,107
[45] Date of Patent: * Sep. 3, 1991

[54] USE OF QUINOLINE DERIVATIVES FOR THE PROTECTION OF CULTIVATED PLANTS

[75] Inventor: Adolf Hubele, Magden, Switzerland

[73] Assignee: Ciba-Geigy Corporation, Ardsley, N.Y.

[*] Notice: The portion of the term of this patent subsequent to Jul. 19, 2005 has been disclaimed.

[21] Appl. No.: 277,530

[22] Filed: Nov. 28, 1988

Related U.S. Application Data

[60] Continuation of Ser. No. 895,627, Sep. 25, 1986, abandoned, which is a division of Ser. No. 465,740, Feb. 11, 1983, Pat. No. 4,623,727.

[30] Foreign Application Priority Data

Feb. 17, 1982 [CH] Switzerland ............... 980/82

[51] Int. Cl.$^5$ ............................ A01N 43/42
[52] U.S. Cl. ............................ 71/94; 71/88; 71/90; 71/92; 71/93; 71/118
[58] Field of Search ............. 71/94, 92, 90, 88, 93, 71/118; 546/177

[56] References Cited

U.S. PATENT DOCUMENTS 4,623,727 11/1986 Hübele ............................ 71/94
4,758,264 11/1986 Hübele ............................ 71/92

OTHER PUBLICATIONS

Areschka et al., "Aryloxyalkylamidoximes with Antiaggressive Etc.", C.A. 84 (1976), No. 144794u.

Alex Areschka et al., Eur. J. Med. Chem-Chimica Therapeutica (1975), pp. 463–469.

Primary Examiner—Glennon H. Hollrah
Assistant Examiner—John D. Pak
Attorney, Agent, or Firm—Edward McC. Roberts

[57] ABSTRACT

A process for the protection of cultivated plants against harmful effects of aggressive agricultural chemicals by the use of compounds of the formula I

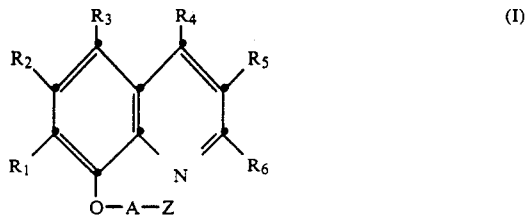

wherein
$R_1$, $R_2$ and $R_3$ independently of one another are each hydrogen, halogen, $C_1$-$C_3$-alkyl, $C_1$-$C_3$-alkoxy, nitro or cyano,
$R_4$, $R_5$ and $R_6$ independently of one another are each hydrogen, halogen or $C_1$-$C_3$-alkyl,
A is any one of the groups —$CH_2$—, —$CH_2$—$CH_2$— or —$CH(CH_3)$—, and
Z is cyano, or amidoxime which can be acylated on the oxygen atom, including acid addition salts and metal complexes thereof.

17 Claims, No Drawings

USE OF QUINOLINE DERIVATIVES FOR THE PROTECTION OF CULTIVATED PLANTS

This application is a continuation of application Ser. No. 895,627 filed Sept. 25, 1986, now abandoned, which is a division of application Ser. No. 465,740, filed Feb. 11, 1983, now U.S. Pat. No. 4,623,727, issued Nov. 18, 1986.

The present invention relates to the use of quinoline derivatives for the protection of cultivated plants against harmful effects of aggressive agricultural chemicals, to compositions containing these quinoline derivatives, to novel quinoline derivatives, and to the production thereof.

With the use of aggressive agricultural chemicals, such as plant protection products, especially herbicides, the cultivated plants frequently suffer damage which is not insignificant. In order to overcome this problem, there have already been suggested compositions which are intended to lessen or prevent these unfavourable effects on the cultivated plants. Plant protection compositions containing nitrile and oxime derivatives of aryloxyalkanecarboxylic acids have thus been described in the German Offenlegungsschrift No. 3,000,076.

It has now been found that surprisingly a group of quinoline derivatives is excellently suitable for protecting cultivated plants against the harmful effects of aggressive agricultural chemicals, for example plant protective compositions, particularly herbicides. These quinoline derivatives are denoted in the following by the term "antidote".

Quinoline derivatives which are suitable for protecting cultivated plants against the harmful effects of aggressive agricultural chemicals correspond to the formula I

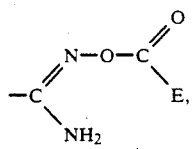

wherein
$R_1$, $R_2$ and $R_3$ independently of one another are each hydrogen halogen, $C_1$-$C_3$-alkyl, $C_1$-$C_3$-alkoxy, nitro or cyano,
$R_4$, $R_5$ and $R_6$ independently of one another are each hydrogen, halogen or $C_1$-$C_3$-alkyl,
A is a group —$CH_2$—, —$CH_2$—$CH_2$— or —$CH(CH_3)$—, and
Z is cyano or amidoxime which can be acylated on the oxygen atom,
including acid addition salts and metal complexes thereof.

By amidoxime is meant the group

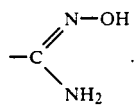

The amidoxime can be acylated on the oxygen atom. Amidoximes acylated on the oxygen atom are those of the formula

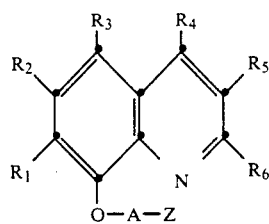

in which E is —$R_7$, —$OR_8$, —$SR_9$ —$NR_{10}R_{11}$, where $R_7$ is $C_1$-$C_7$-alkyl which is unsubstituted or is substituted by halogen or $C_1$-$C_4$-alkoxy, or $R_7$ is $C_3$-$C_6$-cycloalkyl, $C_2$-$C_4$-alkenyl, phenyl which is unsubstituted or substituted by halogen, nitro or $C_1$-$C_3$-alkyl, or it is benzyl which is unsubstituted or substituted by halogen, nitro or $C_1$-$C_3$-alkyl, or $R_7$ is a 5- or 6-membered heterocyclic ring which contains one or two hetero atoms from the group N, O and S, and which is unsubstituted or substituted by halogen; and $R_8$, $R_9$ and $R_{10}$ independently of one another are each $C_1$-$C_8$-alkyl which is unsubstituted or substituted by halogen, or each are $C_2$-$C_4$-alkenyl, $C_3$-$C_6$-alkynyl, phenyl which is unsubstituted or substituted by halogen, $C_1$-$C_3$-alkyl, $C_1$-$C_3$-alkoxy, trifluoromethyl or nitro, or they are each benzyl which is unsubstituted or substituted by halogen or nitro, $R_{11}$ is hydrogen, $C_1$-$C_8$-alkyl or $C_1$-$C_3$-alkoxy, or $R_{10}$ and $R_{11}$ together with the nitrogen atom to which they are bound form a 5- or 6-membered heterocyclic radical which can contain a further hetero atom from the group N, O and S.

As a heterocyclic ring, $R_7$ can be a saturated, partially saturated or unsaturated heterocyclic compound, for example thiophene, furan, tetrahydrofuran and pyrimidine.

Heterocyclic radicals which are formed by $R_{10}$ and $R_{11}$ jointly with the nitrogen atom to which they are bound are saturated, partially saturated or unsaturated heterocyclic radicals. Examples of such heterocyclic radicals are: pyrrolidine, pyrroline, pyrrole, imidazolidine, imidazoline, imidazole, piperazine, pyridine, pyrimidine, pyrazine, thiazine, oxazole, thiazole and particularly piperidine and morpholine.

Suitable as salt formers are organic and inorganic acids. Examples of organic acids are: acetic acid, trichloroacetic acid, oxalic acid, benzenesulfonic acid and methanesulfonic acid; and examples of inorganic acids are: hydrochloric acid, hydrobromic acid, hydriodic acid, sulfuric acid, phosphoric acid, phosphorous acid and nitric acid.

Suitable metal-complexing agents are for example: elements of the 3rd and 4th main groups, such as aluminium, tin and lead, as well as of the 1st to 8th subgroups, such as chromium, manganese, iron, cobalt, nickel, zirconium, zinc, copper, silver and mercury. The subgroup elements of the 4th period are preferred.

Halogen, as substituent or part of a substituent, is in this case fluorine, chlorine, bromine or iodine.

Alkyl, as substituent or part of a substituent, embraces, within the limits of the stated number of carbon atoms, all straight-chain and all branched-chain alkyl groups.

$C_3$-$C_6$-cycloalkyl is cyclopropyl, cyclobutyl, cyclopentyl and cyclohexyl.

To be mentioned among the $C_2$-$C_4$-alkenyl and $C_3$-$C_6$-alkynyl groups are in particular: vinyl, allyl, 1-propenyl, isopropenyl and propynyl.

Particularly suitable for application according to the invention are compounds of the formula I in which $R_1$, $R_2$ and $R_3$ independently of one another are each hydrogen, halogen, $C_1$-$C_3$-alkyl, $C_1$-$C_3$-alkoxy, nitro or cyano; $R_4$, $R_5$ and $R_6$ independently of one another are each hydrogen, halogen or $C_1$-$C_3$-alkyl; A is any one of the groups: —$CH_2$—, —$CH_2$—$CH_2$ or —$CH(CH_3)$—; and Z is cyano or one of the groups

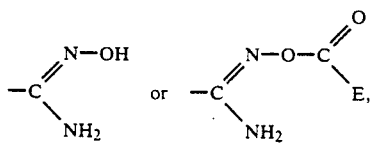

wherein E is —$R_7$, —$OR_8$, —$SR_9$ or —$NR_{10}R_{11}$, where $R_7$ is $C_1$-$C_7$-alkyl which is unsubstituted or substituted by halogen or $C_1$-$C_4$-alkoxy, or $R_7$ is $C_3$-$C_6$-cycloalkyl, $C_2$-$C_4$-alkenyl, phenyl which is unsubstituted or substituted by halogen, nitro or $C_1$-$C_3$-alkyl, or it is benzyl which is unsubstituted or substituted by halogen, nitro or $C_1$-$C_3$-alkyl, or $R_7$ is a 5- or 6-membered heterocyclic ring which contains one or two hetero atoms from the group N, O and S, and which is unsubstituted or substituted by halogen, $R_8$, $R_9$ and $R_{10}$ independently of one another are each $C_1$-$C_8$-alkyl which is unsubstituted or substituted by halogen, or each are $C_2$-$C_4$-alkenyl, $C_3$-$C_6$-alkynyl, phenyl which is unsubstituted or substituted by halogen, $C_1$-$C_3$-alkyl, $C_1$-$C_3$-alkoxy, trifluoromethyl or nitro, or each are benzyl which is unsubstituted or substituted by halogen or nitro, $R_{11}$ is hydrogen, $C_1$-$C_8$-alkyl or $C_1$-$C_3$-alkoxy, or $R_{10}$ and $R_{11}$ jointly with the nitrogen atom to which they are bound form a 5- or 6-membered heterocyclic radical which can contain a further hetero atom from the group N, O and S; including acid addition salts and metal complexes thereof.

Preferred of these compounds are those wherein $R_1$ is hydrogen, chlorine, bromine, iodine or nitro; $R_2$ is hydrogen; $R_3$ is hydrogen, fluorine, chlorine, bromine, iodine, $C_1$-$C_3$-alkyl or nitro; $R_4$ is hydrogen, bromine or methyl; $R_5$ is hydrogen; $R_6$ is hydrogen or methyl; A is —$CH_2$—, —$CH_2$—$CH_2$— or —$CH(CH_3)$—; and Z is cyano,

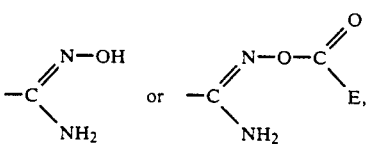

wherein E is —$R_7$, —$OR_8$, —$SR_9$ or —$NR_{10}R_{11}$, where $R_7$ is $C_1$-$C_7$-alkyl, $C_1$-$C_3$-alkyl which is substituted by 1 to 3 chlorine or bromine atoms, or it is $C_1$-$C_4$-alkoxymethyl, $C_3$-$C_6$-cycloalkyl, $C_2$-$C_3$-alkenyl, phenyl which is unsubstituted or substituted by one or two substituents from the group chlorine, nitro and methyl, or it is benzyl which is unsubstituted or monosubstituted by chlorine or nitro, or it is a thiophene, furan, tetrahydrofuran or pyrimidine ring each of which is unsubstituted or mono- or disubstituted by chlorine or bromine $R_8$ is $C_1$-$C_4$-alkyl, ethyl which is monosubstituted by chlorine or bromine, or it is $C_2$-$C_3$-alkenyl, propynyl, phenyl which is unsubstituted or monosubstituted by nitro, or it is benzyl which is unsubstituted or monosubstituted by nitro, $R_9$ is $C_1$-$C_7$-alkyl, $R_{10}$ is $C_1$-$C_4$-alkyl, chloroethyl, or phenyl which is unsubstituted or substituted by one or two substituents from the group chlorine, methoxy or trifluoromethyl, and $R_{11}$ is hydrogen, methyl or methoxy, or $R_{10}$ and $R_{11}$ jointly with the nitrogen atom to which they are bound form a piperidine or morpholine ring.

More especially preferred is the use of compounds of the formula I wherein $R_1$ is hydrogen, chlorine, bromine or iodine; $R_2$ is hydrogen; $R_3$ is hydrogen, chlorine or nitro; $R_4$ and $R_5$ are hydrogen; $R_6$ is hydrogen or methyl; A is —$CH_2$—, —$CH_2$—$CH_2$— or —$CH(CH_3)$—; and Z is cyano,

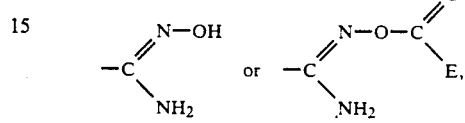

wherein E is —$R_7$, —$OR_8$, —$SR_9$ or —$NR_{10}R_{11}$, where $R_7$ is methyl, ethyl, n-propyl, isopropyl, n-butyl, tert-butyl, isobutyl, chloromethyl, bromomethyl, 2-chloroethyl, 3-chloro-n-propyl, 1,2-dichloroethyl, methoxymethyl, n-propoxymethyl, sec-butoxymethyl, cyclopropyl, vinyl, 1-propenyl, isopropenyl, phenyl, 2-chlorophenyl, 4-chlorophenyl, benzyl, 2-thienyl, 2-furyl, 5-bromo-2-furyl, 2-tetrahydrofuryl or 2,4-dichloropyrimidin-5-yl, $R_8$ is methyl, ethyl, n-propyl, n-butyl, 2-bromoethyl, allyl, phenyl or benzyl, $R_9$ is ethyl, isopropyl or n-pentyl, $R_{10}$ is methyl, ethyl, isopropyl, n-butyl, phenyl, 3-trifluoromethylphenyl, 4-chlorophenyl or 2,5-dichlorophenyl, and $R_{11}$ is hydrogen or methoxy.

Compounds of this group to be particularly emphasised are those wherein $R_1$ is hydrogen, chlorine, bromine or iodine; $R_2$ is hydrogen; $R_3$ is hydrogen or chlorine; $R_4$ and $R_5$ are hydrogen; $R_6$ is hydrogen or methyl; A is —$CH_2$—; and Z is cyano,

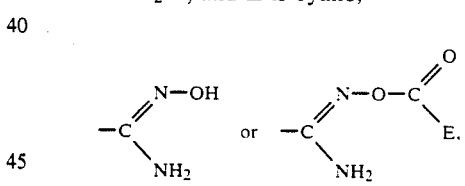

wherein E is $R_7$, —$OR_8$ or —$NR_{10}R_{11}$, where $R_7$ is chloromethyl, $R_8$ is methyl, $R_{10}$ is isopropyl, and $R_{11}$ is hydrogen.

Individual compounds to be preferably used are:
8-(cyanomethoxy)-quinoline,
2-(8-quinolinoxy)-acetamide oxime,
2-methyl-8-(cyanomethoxy)-quinoline,
2-(2-methyl-8-quinolinoxy)-acetamide oxime,
2-(5-chloro-8-quinolinoxy)-acetamide oxime,
0-(isopropylaminocarbonyl)-2-(8-quinolinoxy)-acetamide oxime,
5-chloro-7-bromo-8-(cyanomethoxy)-quinoline,
0-(chloromethylcarbonyl)-2-(8-quinolinoxy)-acetamide oxime,
2-(5-chloro-7-bromo-8-quinolinoxy)-acetamide oxime,
2-(5-chloro-7-iodo-8-quinolinoxy)-acetamide oxime
0-(isopropylaminocarbonyl)-2-(5-chloro-7-bromo-8-quinolinoxy)-acetamide oxime,
2-(2-methyl-5,7-dichloro-8-quinolinoxy)-acetamide oxime,
5,7-dichloro-8-(cyanomethoxy)-quinoline, 0-(isopropylaminocarbonyl)-2-(5-chloro-7-iodo-8-quinolinoxy)-acetamide oxime,
2-methyl-5,7-dichloro-8-(cyanomethoxy)-quinoline 0-(isopropylaminocarbonyl)-2-(2-methyl-5,7-dichloro-8-quinolinoxy)-acetamide oxime;
and in particular:
5-chloro-7-iodo-8-(cyanomethoxy)-quinoline,
5-chloro-8-(cyanomethoxy)-quinoline, and
0-(methoxycarbonyl)-2-(8-quinolinoxy)-acetamide oxime.

Aggressive agricultural chemicals are for example: defoliating agents, desiccants, agents for protection against frost damage, and plant protection products, for example insecticides, fungicides, bactericides, nematocides and especially herbicides. The agricultural chemicals can belong to various classes of substances. Herbicides can belong for example to one of the following classes: triazines and triazinones; ureas, for example 1-(benzothiazol-2-yl)-1,3-dimethylurea ("Methabenzthiazuron"), or in particular phenylureas or sulfonylureas; carbamates and thiocarbamates, haloacetanilides, especially chloroacetanilides; chloroacetamides; halophenoxyacetic acid esters; diphenyl ethers, such as substituted phenoxyphenoxyacetic acid esters and -amides, and substituted phenoxyphenoxypropionic acid esters and -amides; substituted pyridyloxyphenoxyacetic acid esters and -amides and substituted pyridyloxyphenoxypropionic acid esters and -amides, particularly 2-[4-(3,5-dichloropyridyl-2-oxy)phenoxy]-propionic acid-2-propynyl ester and 2-[4-(5-trifluoromethylpyridyl-2-oxy)-phenoxy]-propionic acid-n-butyl ester; benzoic acid derivatives; nitroanilines; oxadiazolones, phosphates; and pyrazoles.

The substances specified below are examples of those coming into consideration:

triazines and triazinones: 2,4-bis(isopropylamino)-6-methylthio-1,3,5-triazine ("Prometryne"), 2,4-bis(ethylamino)-6-methylthio-1,3,5-triazine ("Simetryne"), 2-(1',2'-dimethylpropylamino)-4-ethylamino-6-methylthio1,3,5-triazine ("Dimethametryne"), 4-amino-6tert-butyl4,5-dihydro-3-methylthio-1,2,4-triazin-5-one ("Metribuzin"), 2-chloro-4-ethylamino-6-isopropylamino-1,3,5-triazine ("Atrazine"), 2-chloro-4,6-bis(ethylamino)-1,3,5-triazine ("Simazine"), 2-tert-butylamino-4-chloro-6-ethylamino-1,3,5triazine ("Terbuthylazine"), 2-tert-butylamino-4-ethylamino-6-methoxy-1,3,5-triazine ("Terbumeton"), 2-tert-butylamino-4-ethylamino-6-methylthio-1,3,5-triazine ("Terbutryne"), 2-ethylamino-4-isopropylamino-6-methylthio1,3,5-triazine ("Ametryne");

ureas: 1-(benzothiazol-2-yl)-1,3-dimethylurea; phenylureas, for example 3-(3-chloro-p-tolyl)-1,1-dimethylurea ("Chlortoluron"), 1,1-dimethyl-3-(ααα-trifluoro-m-tolyl)urea ("Fluometuron"), · 3-(4-bromo-3-chlorophenyl)-1-methoxy-1-methylurea ("Chlorbromuron"), 3-(4-bromophenyl)-1-methoxy-1-methylurea ("Metobromuron"), 3-(3,4-dichlorophenyl)-1-methoxy-1-methylurea ("Linuron"), 3-(4-chlorophenyl)-1-methoxy-1-methylurea ("Monolinuron"), 3-(3,4-dichlorophenyl)-1,1-dimethylurea ("Diuron"), 3-(4-chlorophenyl)-1,1-dimethylurea ("Monuron"), 3-(3-chloro-4-methoxyphenyl)-1,1-dimethylurea ("Metoxuron"); sulfonylureas, for example N-(2-chlorophenylsulfonyl)-N'-(4-methoxy-6-methyl-1,3,5-triazin-2-yl)-urea, N-(2-methoxycarbonylphenylsulfonyl)-N'(4,6-dimethylpyrimidin-2yl)-urea, N-(2,5-dichlorophenyl-sulfonyl)-N'-(4,6-dimethoxypyrimidin-2-yl)-urea, N-[2-(2-butenyloxy)-phenylsulfonyl]-N'-(4-methoxy-6-methyl-1,3,5-triazin-2-yl)-urea, and also the sulfonylureas mentioned in the European Patent Publications Nos. 44808 and 44809;

carbamates and thiocarbamates: N-(3',4'-dichlorophenyl)propionanilide ("Propanil"), S-4-chlorobenzyl-diethylthiocarbamate ("Benthiocarb"), S-ethyl-N,N-hexamethylenethiocarbamate ("Molinate"), S-ethyl-dipropyl-thiocarbamate ("EPTC"), N,N-di-sec-butyl-S-benzyl-thiocarbamate, S-(2,3-dichlorallyl)-di-isopropyl-thiocarbamate ("Di-allate"), 1-(propylthiocarbonyl)-decahydro-quinaldine, S-ethyl-di-isobutyl-thiocarbamate ("Butylate"); · chloroacetanilides: 2-chloro-2',6'-diethyl-N-(2''-n-propoxyethyl)-acetanilide ("Propalochlor"), 2-chloro-6'-ethyl-N-2''-methoxy-1''-methylethyl)-acet-o-toluidide ("Metolachlor"), 2-chloro-2',6'-diethyl-N-(butoxymethyl)acetanilide ("Butachlor"), 2-chloro-6'-ethyl-N-(ethoxymethyl)acet-o-toluidide ("Acetochlor"), 2-chloro-6'-ethyl-N-(2''-propoxy-1''-methylethyl)acet-o-toluidide, 2-chloro-2',6'-dimethyl-N-(2''-methoxy-1''-methylethyl)acetanilide, 2-chloro-2',6'-dimethyl-N-(2''-methoxyethyl)acetanilide ("Dimethachlor"), 2-chloro-2',6'-diethyl-N-(pyrazol-1-yl-methyl)acetanilide, 2-chloro-6'-ethyl-N-(pyrazol-1-yl-methyl)acet-o-toluidide, 2-chloro-6'-ethyl-N-(3,5-dimethylpyrazol-1-ylmethyl)acet-o-toluidide, 2-chloro-6'-ethyl-N-(2''-butoxy-1''-methylethyl)acet-o-toluidide ("Metazolachlor"), 2-chloro-6'-ethyl-N-(2''-butoxyl-1''-(methylethyl)-acet-o-toluidide and 2-chloro-2'-trimethylsilyl-N-(butoxymethyl)acetanilide;

chloroacetamides: N-[1-isopropyl-2-methylpropen-1-yl-(1)]-N-(2'-methoxyethyl)-chloroacetamide;

diphenyl ethers and nitrodiphenyl ethers: 2,4-dichlorophenyl-4'-nitrophenyl ether ("Nitrofen"), 2-chloro-1-(3'-ethoxy-4'-nitrophenoxy)-4-trifluoromethyl-benzene ("Oxyfluorfen"), 2',4'-dichlorophenyl-3-methoxy-4-nitrophenyl ether ("Chlormethoxynil"), 2-[4'-(2'',4''-dichlorophenoxy)phenoxy]-propionic acid-methyl ester, N-(2'-phenoxyethyl)-2-[5'(2''-chloro-4''-trifluoromethylphenoxy)-phenoxy]-propionic acid amide, 2-[2-nitro-5-(2-chloro-4-trifluoromethylphenoxy)-phenoxy]-propionic acid-2-methoxyethyl ester; 2-chloro-4-trifluoromethylphenyl-3'-oxazolin-2'-yl-4'-nitrophenyl ether;

benzoic acid derivatives: methyl-5-(2',4'-dichloro-phenoxy)-2-nitrobenzoate ("Bifenox"), 5-(2'-chloro-4'-trifluoromethylphenoxy)-2-nitorbenzoic acid ("Acifluorfen"), 2,6-dichlorobenzonitrile ("Dichlobenil");

nitroanilines: 2,6-dinitro-N,N-dipropyl-4-trifluoromethylaniline ("Trifluralin"), N-(1'-ethylpropyl)-2,6-dinitro3,4-xylidine ("Pendimethalin");

oxadiazolones: 5-tert-butyl-3-(2',4'-dichloro-5'-isopropoxyphenyl)-1,3,4-oxadiazol-2-one ("Oxadiazon");

phosphates: S-2-methylpiperidino-carbonylmethyl-O,O-dipropylphosphorodithioate ("Piperophos"); and pyrazoles: 1,3-dimethyl-4-(2',4'-dichlorobenzoyl)-5-(4'tolylsulfonyloxy)-pyrazole.

The compounds of the formula I are particularly suitable for protecting cultivated plants against harmful effects of herbicides of the formula A

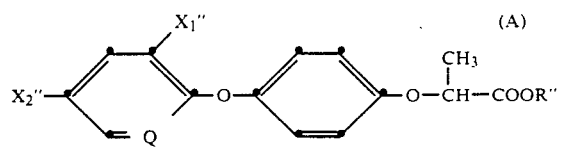

wherein
X″₁ is hydrogen or halogen,
X″₂ is hydrogen, halogen or trifluoromethyl,
Q is the fragment =N- or =CH-,
R″ is $C_1$–$C_4$-alkyl which is unsubstituted or substituted by $C_1$–$C_4$-alkoxy, or it is $C_3$–$C_4$-alkenyl, $C_3$–$C_4$-alkynyl or

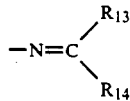

where $R_{13}$ is $C_1$–$C_4$-alkyl, $R_{14}$ is $C_1$–$C_4$-alkyl, or $R_{13}$ and $R_{14}$ together are $C_1$–$C_5$-alkylene.

Cultivated plants which can be protected by quinoline derivatives of the formula I against aggressive agricultural chemicals are in particular those which are of importance in the foodstuffs and textile fields, for example cultivated millet, rice, maize, varieties of cereals (wheat, rye, barley, oats, and so forth), cotton, sugar beet sugar cane and soya bean.

A suitable process for protecting cultivated plants by the use of compounds of the formula I comprises treating cultivated plants, parts of these plants, or soils intended for the cultivation of the cultivated plants, before or after introduction of the vegetable material into the soil, with a compound of the formula I or with a composition containing such a compound. The treatment can be carried out before, simultaneously with or after the application of the agricultural chemicals. Parts of plants concerned are especially those which are capable of the new formation of a plant, for example seeds, fruits, stems and branches (cuttings), as well as roots, tubers and rhizomes.

The invention relates also to a process for the selective controlling of weeds in crops of cultivated plants, in which process the cultivated plants, parts of the cultivated plants, or cultivated areas for cultivated plants, are treated with a herbicide and a compound of the formula I or Ia, or with a composition containing this combination. The compositions which contain the herbicide/antidote combination likewise form subject matter of the present invention.

The weeds to be controlled can be both monocotyledonous and dicotyledonous weeds.

Cultivated plants or parts of these plants to be protected are for example those mentioned in the foregoing. The cultivated areas concerned are those on which cultivated plants are already growing, or sown areas of land, and also the soil intended for the growing of cultivated plants.

The amount of antidote to be applied in proportion to the amount of agricultural chemical depends largely upon the type of application. In the case of a field treatment, which is carried out either with the use of a tank mixture or with a separate application of agricultural chemical and antidote, the employed ratio of antidote to agricultural chemical is as a rule from 1:100 to 10:1, preferably 1:5 to 8:1, and particularly 1:1.

With seed dressing and similar methods of application, however, the amounts of antidote required in proportion to the amounts of agricultural chemical applied per hectare of cultivated land are much smaller. There are used for seed dressing as a rule 0.1 to 10 g of antidote per kg of seed, preferably 1 to 2 g. When the antidote is applied shortly before sowing, with seed swelling, there are advantageously used antidote solutions containing the active ingredient at a concentration of 1 to 10,000 ppm, preferably 100 to 1000 ppm.

The compounds of the formula I can be used on their own or together with inert additives and/or the agricultural chemicals to be antagonised.

The present application relates therefore also to compositions which contain compounds of the formula I and inert additives and/or agricultural chemicals to be antagonised, especially plant protection agents, in particular herbicides.

For application, the compounds of the formula I, or combinations of compounds of the formula I with the agricultural chemicals to be antagonised, are advantageously used together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active ingredient of the formula I, or a combination of active ingredient of the formula I and agricultural chemicals to be antagonised, and optionally a solid or liquid additive, are produced in a known manner, for example by the intimate mixing and/or grinding of the active ingredients with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pre-granulated materials of inorganic or organic nature, such as in particular dolomite or ground plant residues.

Suitable surface-active compounds are, depending on the nature of the active ingredient of the formula I to be formulated, and optionally also of the agricultural chemical to be antagonised, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual",
MC Publishing Corp., Ringwood, N.J., 1980, and
Sisely and Wood, "Encyclopedia of Surface Active Agents", Chemical Publishing Co., Inc., N.Y., 1980.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside. Whereas commercial products are preferably in the form of concentrated compositions, the compositions employed by the end-user are as a rule diluted.

The compositions can also contain further additives, such as stabilisers, antifoam agents, viscosity regulators, binders and adhesives, as well as fertilisers or other active substances for obtaining special effects.

For the use of compounds of the formula I, or of compositions containing them, for the protection of cultivated plants against the harmful effects of aggressive agricultural chemicals, various methods and techniques are applicable, such as those described in the following.

i) Seed dressing a) Dressing of the seeds with an active ingredient, formulated as a wettable powder, by shaking in a vessel until there is a uniform distribution over the surface of the seeds (dry dressing). The amount of active ingredient of the formula I used for this purpose is about 10 to 500 g (40 g to 2 kg of wettable powder) per 100 kg of seed.

b) Dressing of the seeds with an emulsion concentrate of the active ingredient of the formula I according to method a) (wet dressing).

c) Dressing by immersion of the seed in a liquor containing 50–3200 ppm of active ingredient of the formula I for 1 to 72 hours, and optionally subsequent drying of the seed (immersion dressing).

The dressing of the seed or the treatment of the germinated young seedlings is, in accordance with nature, the preferred method of application, because the treatment with the active ingredient is directed completely at the target growth. There are used as a rule 10 g to 500 g, preferably 50 to 250 g of active substance (AS) per 100 kg of seed, whereby, depending on the method of treatment, which may render possible also the addition of other active substances or micronutrients, the stated limiting concentrations can be varied upwards or downwards (repeat dressing).

ii) Application as tank mixture

A liquid preparation of a mixture of antidote and herbicide (quantitative ratio between 10:1 and 1:10) is used, the applied amount of herbicide being 0.1 to 10 kg per hectare. This tank mixture is preferably applied before or immediately after sowing, or it is worked into the unsown soil to a depth of 5 to 10 cm.

iii) Application into the seed furrow

The antidote is introduced, as an emulsion concentrate, wettable powder or granulate, into the open sown seed furrow, and, after the covering of the seed furrow in the normal manner, the herbicide is applied before emergence of the plants.

iv) Controlled release of active ingredient

The active ingredient is absorbed, in solution, onto mineral granular carriers or polymerised granulates (urea/formaldehyde), and the material is allowed to dry. A coating can if required be applied (coated granules), which enables the active ingredient to be released in controlled amounts over a certain period of time.

Compounds of the formula I in which at the same time $R_1$, $R_2$, $R_4$, $R_5$ and $R_6$ are hydrogen, $R_3$ is hydrogen or chlorine, A is one of the groups —CH$_2$— or —CH(CH$_3$)— and Z is cyano or the group

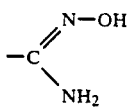

are known from Areschka et al., Eur. J. Chem. - Chimica Therapeutica, September–October 1975, 10, (5), 463–469. Some of these compounds have antiaggressive properties.

The remaining compounds of the formula I are novel and are subject matter of the present invention. They correspond to the formula Ia

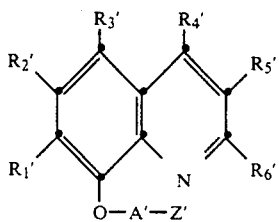

wherein
R'$_1$, R'$_2$ and R'$_3$ independently of one another are each hydrogen, halogen, C$_1$-C$_3$-alkyl, C$_1$-C$_3$-alkoxy, nitro or cyano,
R'$_4$, R'$_5$ and R'$_6$ independently of one another are each hydrogen, halogen or C$_1$-C$_3$-alkyl,
A' is any one of the groups —CH$_2$—, —CH$_2$—CH$_2$— or —CH(CH$_3$)—, and
Z' is cyano or amidoxime which can be acylated on the oxygen atom,
including acid addition salts and metal complexes thereof, with the proviso that Z' is not cyano or amidoxime when simultaneously R'$_1$, R'$_2$, R'$_4$, R'$_5$ and R'$_6$ are hydrogen, R'$_3$ is hydrogen or chlorine, and A' is —CH$_2$— or —CH(CH$_3$)—.

Preferred compounds of the formula Ia are those wherein
R'$_1$, R'$_2$ and R'$_3$ independently of one another are each hydrogen, halogen, C$_1$-C$_3$-alkyl, C$_1$-C$_3$-alkoxy, nitro or cyano,
R'$_4$, R'$_5$ and R'$_6$ independently of one another are each hydrogen, halogen or C$_1$-C$_3$-alkyl,
A' is any one of the groups —CH$_2$—, —CH$_2$—CH$_2$— or —CH(CH$_3$)—, and
Z' is cyano or either one of the groups

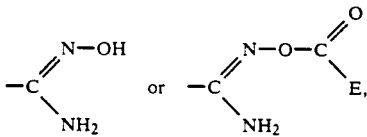

in which E is —R$_7$, —OR$_8$, —SR$_9$ or —NR$_{10}$R$_{11}$, is C$_1$-C$_7$-alkyl which is unsubstituted or substituted by halogen or C$_1$-C$_4$-alkoxy, or R$_7$ is C$_3$-C$_6$-cycloalkyl, C$_2$-C$_4$-alkenyl, phenyl which is unsubstituted or substituted by halogen, nitro or C$_1$-C$_3$-alkyl, or it is benzyl which is unsubstituted or substituted by halogen, nitro or C$_1$-C$_3$-alkyl, or R$_7$ is a 5- or 6-membered heterocyclic ring which contains one or two hetero atoms from the group N, O, and S, and which is unsubstituted or substituted by halogen; and R$_8$, R$_9$ and R$_{10}$ independently of one another are each C$_1$-C$_8$-alkyl which is unsubstituted or substituted by halogen, or each are C$_2$-C$_4$-alkenyl, C$_3$-C$_6$-alkynyl, phenyl which is unsubstituted or substituted by halogen, C$_1$-C$_3$-alkyl, C$_1$-C$_3$-alkoxy, trifluoromethyl or nitro, or they are each benzyl which is unsubstituted or substituted by halogen or nitro, R$_{11}$ is hydrogen, C$_1$-C$_8$-alkyl or C$_1$-C$_3$-alkoxy, or R$_{10}$ and R$_{11}$ together with the nitrogen atom to which they are bound form a 5- or 6-membered heterocyclic radical which can also contain a further hetero atom from the group N, O and S;
including acid addition salts and metal complexes thereof, with the proviso that Z' is not cyano or amidoxime when simultaneously R'$_1$, R'$_2$, R'$_4$, R'$_5$ and R'$_6$ are hydrogen, R'$_3$ is hydrogen or chlorine, and A' is —CH$_2$— or —CH(CH$_3$)—.

Preferred compounds of this group are those wherein R'$_1$ is hydrogen, chlorine, bromine, iodine or nitro, R'$_2$ is hydrogen, R'$_3$ is hydrogen, fluorine, chlorine, bromine, iodine, C$_1$-C$_3$-alkyl or nitro, R'$_4$ is hydrogen, bromine or methyl, R'$_5$, is hydrogen, R'$_6$ is hydrogen or methyl, A' is —CH$_2$—, —CH$_2$—CH$_2$— or —CH(CH$_3$)—, and Z' is cyano,

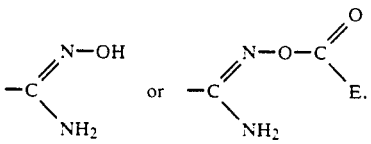

in which E is —R$_7$, —OR$_8$, —SR$_9$ or —NR$_{10}$R$_{11}$, wherein R$_7$ is C$_1$-C$_7$-alkyl, C$_1$-C$_3$-alkyl which is substituted by 1 to 3 chlorine or bromine atoms, or R$_7$ is C$_1$-C$_4$-alkoxymethyl, C$_3$-C$_6$-cycloalkyl, C$_2$-C$_3$-alkenyl, phenyl which is unsubstituted or substituted by one or two substituents from the group chlorine, nitro and methyl, or it is benzyl which is unsubstituted or monosubstituted by chlorine or nitro, or R$_7$ is a thiophene, furan, tetrahydrofuran or pyrimidine ring each of which is unsubstituted or mono- or disubstituted by chlorine or bromine, R$_8$ is C$_1$-C$_4$-alkyl, ethyl monosubstituted by chlorine or bromine, or it is C$_2$-C$_3$-alkenyl, propynyl, phenyl which is unsubstituted or monosubstituted by nitro, or it is benzyl which is unsubstituted or monosubstituted by nitro, R$_9$ is C$_1$-C$_7$-alkyl, R$_{10}$ is C$_1$-C$_4$-alkyl, chloroethyl, or phenyl which is unsubstituted or substituted by one or two substituents from the group chlorine, methoxy and trifluoromethyl, and R$_{11}$ is hydrogen, methyl or methoxy, or R$_{10}$ and R$_{11}$ jointly with the nitrogen atom to which they are bound form a piperidine or morpholine ring, with the proviso that Z' is not cyano or amidoxime when simultaneously R'$_1$, R'$_2$, R'$_4$, R'$_5$ and R'$_6$ are hydrogen, R'$_3$ is hydrogen or chlorine, and A' is —CH$_2$— or —CH(CH$_3$)—.

Compounds of this group to be emphasised are in particular those in which R'$_1$ is hydrogen, chlorine, bromine or iodine, R'$_2$ is hydrogen, R'$_3$ is hydrogen, chlorine or nitro, R'$_4$ and R'$_5$ are hydrogen, R'$_6$ is hydrogen or methyl, A' is —CH$_2$—, —CH$_2$—CH$_2$— or —CH(CH$_3$)— and Z' is cyano,

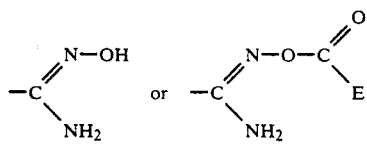

in which E is —R$_7$, —OR$_8$, —SR$_9$ or —NR$_{10}$R$_{11}$, wherein R$_7$ is methyl, ethyl, n-propyl, isopropyl, n-butyl, tert-butyl, isobutyl, chloromethyl, bromomethyl, 2-chloroethyl, 3-chloro-n-propyl, 1,2-dichloroethyl, methoxymethyl, n-propoxymethyl, sec-butoxymethyl, cyclopropyl, vinyl, 1-propenyl, isopropenyl, phenyl, 2-chlorophenyl, 4-chlorophenyl, benzyl, 2-thienyl, 2-furyl, 5-bromo-2-furyl, 2-tetrahydrofuryl or 2,4-dichloropyrimidin-5-yl, R$_8$ is methyl, ethyl, n-propyl, n-butyl, 2-bromoethyl, allyl, phenyl or benzyl, R$_9$ is ethyl, isopropyl or n-pentyl, R$_{10}$ is methyl, ethyl, isopropyl, n-butyl, phenyl, 3-trifluoromethylphenyl, 4-chlorophenyl or 2,5-dichlorophenyl, and R$_{11}$ is hydrogen or methoxy, with the proviso that Z' is not cyano or amidoxime when simultaneously R'$_1$, R'$_2$, R'$_4$, R'$_5$ and R'$_6$ are hydrogen R'$_3$ is hydrogen or chlorine, and A' is —CH$_2$— or —CH(CH$_3$)—.

More especially preferred are compounds of the formula Ia in which R'$_1$ is hydrogen, chlorine, bromine or iodine, R'$_2$ is hydrogen, R'$_3$ is hydrogen or chlorine, R'$_4$ and R'$_5$ are hydrogen, R'$_6$ is hydrogen or methyl, A' is —CH$_2$—, and Z' is cyano,

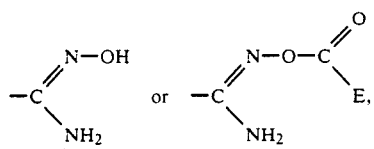

in which E is —R$_7$, —OR$_8$ or —NR$_{10}$R$_{11}$, wherein R$_7$ is chloromethyl, R$_8$ is methyl R$_{10}$ is isopropyl, and R$_{11}$ is hydrogen, with the proviso that Z' is not cyano or amidoxime when simultaneously R'$_1$, R'$_2$, R'$_4$, R'$_5$ and R'$_6$ are hydrogen, R'$_3$ is hydrogen or chlorine, and A' is —CH$_2$—.

The following compounds are to be especially emphasised:
2-methyl-8-(cyanomethoxy)-quinoline,
2-(2-methyl-8-quinolinoxy)-acetamide oxime,
0-(isopropylaminocarbonyl)-2-(8-quinolinoxy)-acetamide oxime,
0-(chloromethylcarbonyl)-2-(8-quinolinoxy)-acetamide oxime,
2-(5-chloro-7-bromo-8-quinolinoxy)-acetamide oxime,
5-chloro-7-bromo-8-(cyanomethoxy)-quinoline,
0(methoxycarbonyl)-2-(8-quinolinoxy)-acetamide oxime,
2-(5-chloro-7-iodo-8-quinolinoxy).acetamide oxime,
0-(isopropylaminocarbonyl)-2-(5-chloro-7-bromo-8-quinolinoxy)-acetamide oxime,
2-(2-methyl-5,7-dichloro-8-quinolinoxy)-acetamide oxime,
5,7-dichloro-8- cyanomethoxy)-quinoline,
0-(isopropylaminocarbonyl)-2-(5-chloro-7-iodo-8-quinolinoxy)-acetamide oxime,
2-methyl-5,7-dichloro-8-(cyanomethoxy)-quinoline,
0-(isopropylaminocarbonyl)-2-(2-methyl-5,7-dichloro-8-quinolinoxy)-acetamide oxime,
and in particular
5-chloro-7-iodo-8-(cyanomethoxy)-quinoline.

Compounds of the formula Ia are produced by the following procedures:

a) compounds of the formula Ia in which R'$_1$, R'$_2$, R'$_3$, R'$_4$, R'$_5$ and R'$_6$ have the meanings defined for the formula Ia, A' is the group —CH$_2$—CH$_2$—, and Z' is cyano, are produced by reacting a compound of the formula II

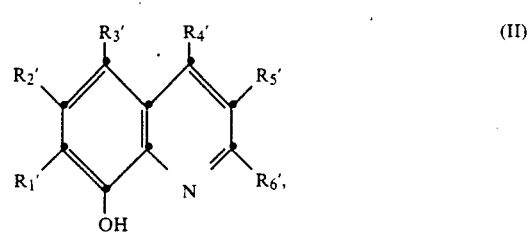

wherein R'$_1$, R'$_2$, R'$_3$, R'$_4$, R'$_5$ and R'$_6$ have the meanings given in the foregoing, with a compound of the formula III

$$CH_2=CH-CN \qquad (III); or$$

b) compound of the formula Ia in which R'$_1$, R'$_2$, R'$_3$, R'$_4$, R'$_5$ and R'$_6$ have the meanings defined under the formula Ia, A' is a group —CH$_2$— or —CH(CH$_3$)—, and Z' is cyano, are produced by reacting a compound of the formula II

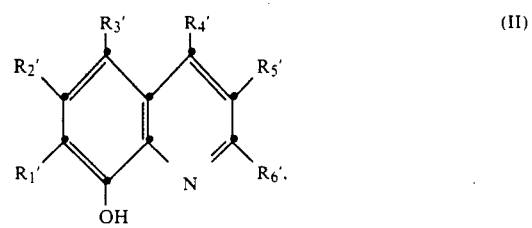

wherein R'$_1$, R'$_2$, R'$_3$, R'$_4$, R'$_5$ and R'$_6$ have the meanings given for the formula II,
i) with a compound of the formula IV

$$Hal-A'-CN \qquad (IV)$$

wherein Hal is a halogen atom, and A' has the meaning defined in the foregoing, or
ii) with a compound of the formula V

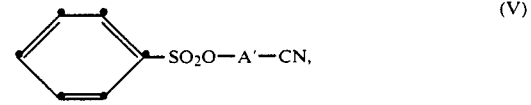

wherein A' has the meaning defined in the foregoing, or
iii) with a compound of the formula VI

$$Hal-A'-COOR_{12} \qquad (VI),$$

wherein Hal is a halogen atom, R$_{12}$ is an alkyl group having 1 to 6 carbon atoms, and A' has the meaning defined in the foregoing; and converting the resulting ester of the formula VII

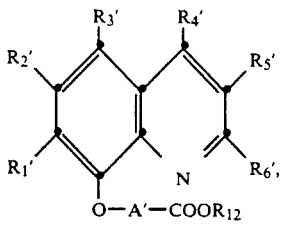

wherein R'$_1$, R'$_2$, R'$_3$, R'$_4$, R'$_5$, R'$_6$, A' and R$_{12}$ have the meanings defined in the foregoing, with ammonia into the corresponding amide of the formula VIII

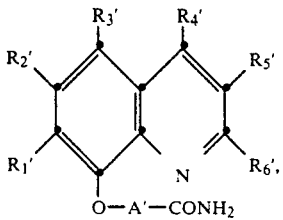

wherein R'$_1$, R'$_2$, R'$_3$, R'$_4$, R'$_5$, R'$_6$, and A' have the meanings defined above, and then dehydrating the product obtained; and/or c) compounds of the formula Ia in which R'$_1$, R'$_2$, R'$_3$, R'$_4$, R'$_5$ R'$_6$ and A' have the meanings defined for the formula Ia, and Z' is amidoxime which can be acylated on the oxygen atom, are produced by reacting a compound of the formula Ia wherein R'$_1$, R'$_2$, R'$_3$, R'$_4$, R'$_5$, R'$_6$ and A' have the meanings defined for the formula Ia, and Z' is cyano, with hydroxylamine or with an acid salt of hydroxylamine; and/or d) compounds of the formula Ia in which R'$_1$, R'$_2$, R'$_3$, R'$_4$, R'$_5$, R'$_6$ and A' have the meanings defined for the formula Ia, and Z' is acylated amidoxime, are produced by acylating a compound of the formula Ia wherein R'$_1$, R'$_2$, R'$_3$, R'$_4$, R'$_5$, R'$_6$ and A' have the meanings given for the formula Ia, and Z' is amidoxime.

Thus, for example, compounds of the formula Ia in which R'$_1$, R'$_2$, R'$_3$, R'$_4$, R'$_5$, R'$_6$ and A' have the meanings defined for the formula Ia, and Z' is acylated amidoxime of the formula

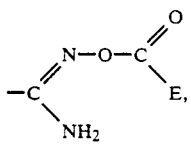

wherein E is —R$_7$, —OR$_8$, —SR$_9$ or —NR$_{10}$R$_{11}$, in which R$_7$ is C$_1$–C$_7$-alkyl which is unsubstituted or substituted by halogen or C$_1$–C$_4$-alkoxy, or R$_7$ is C$_3$–C$_6$-cycloalkyl, C$_2$–C$_4$-alkenyl, phenyl which is unsubstituted or substituted by halogen, nitro or C$_1$–C$_3$-alkyl, or it is benzyl unsubstituted or substituted by halogen, nitro or C$_1$–C$_3$-alkyl, or R$_7$ is a 5- or 6-membered heterocyclic ring which contains one or two hetero atoms from the group N, O and S, and which is unsubstituted or substituted by halogen, R$_8$, R$_9$ and R$_{10}$ independently of one another are each C$_1$–C$_8$-alkyl which is unsubstituted or substituted by halogen, or they are each C$_2$–C$_4$-alkenyl, C$_3$–C$_6$-alkynyl, phenyl which is unsubstituted or substituted by halogen, C$_1$–C$_3$-alkyl, C$_1$–C$_3$-alkyl, C$_1$–C$_3$-alkoxy, trifluoromethyl or nitro, or are each benzyl which is unsubstituted or substituted by halogen or nitro, and R is hydrogen, C$_1$–C$_8$-alkyl or C$_1$–C$_3$-alkoxy, or R$_{10}$ and R$_{11}$ together with the nitrogen atom to which they are bound form a 5- to 6-membered heterocyclic radical which can also contain a further hetero atom from the group N, O and S, can be produced by reacting a compound of the formula Ia, wherein R'$_1$, R'$_2$, R'$_3$, R'$_4$, R'$_5$, R'$_6$ and A' have the meanings defined for the formula Ia, and Z' is amidoxime, with a compound of the formula IX

in which X is a halogen atom, and Y is —R$_7$, —OR$_8$, —SR$_9$ or —NR$_{10}$R$_{11}$, wherein R$_7$, R$_8$, R$_9$, R$_{10}$ and R$_{11}$ have the meanings defined in the foregoing, or X and Y together are the imino group =N—R$_{10}$.

The reaction (a) of compounds of the formula II with compounds of the formula III is preferably performed in the presence of a basic catalyst. Particularly suitable as catalysts are metal alcoholates, especially alkali metal and alkaline-earth metal alcoholates, or hydroxides, for example sodium hydroxide.

The reaction (b/i) of compounds of the formula II with compounds of the formula IV is carried out preferably in methyl ethyl ketone in the presence of potassium carbonate, or in dimethylformamide in the presence of sodium hydride, whilst the reaction (b/ii) of compounds of the formula II with compounds of the formula V is performed most advantageously in a two-phase system, the one phase being water and the other phase being a liquid immiscible with water, such as toluene or methylene chloride. The catalyst used in these reactions is a phase-transfer catalyst, for example benzyltriethylammonium chloride.

In the compounds of the formula IV, Hal is chlorine, bromine, fluorine or iodine. Chlorine and bromine are preferred, the catalyst employed being advantageously potassium iodide.

In the compounds of the formula VI, Hal is chlorine, bromine, iodine or fluorine.

The dehydration (b/iii) of amides of the formula VIII to the corresponding nitriles can be performed in a known manner, for example with phosphorus pentoxide or with phosphorus oxychloride.

Suitable for the reaction (c) of nitriles of the formula Ia with hydroxylamine or with acid salts of hydroxylamine are in particular salts of hydroxylamine with inorganic acids, especially hydroxylamine hydrochloride or hydroxylamine sulfate, the reaction with acid salts being advantageously performed in the presence of a base, for example hydroxides of alkali metals or alkaline-earth metals, such as sodium hydroxide, or tertiary organic bases, for example tertiary amines, such as pyridine or trialkylamine.

In the formula IX, X is chlorine, bromine, fluorine or iodine.

The quinolines and quinaldines to be used as starting products are known, or they can be produced by processes analogous to known processes.

The known compounds of the formula I which are not embraced by the formula Ia can be produced by the methods described for compounds of the formula Ia.

The Examples which follow serve to further illustrate the invention.

Production Examples for active ingredients

Example 1

2-Methyl-5,7-dichloro-8-(cyanomethoxy)-quinoline (Compound No. 18)

10.7 g of 5,7-dichloro-8-hydroxyquinaldine are dissolved at elevated temperature in 150 ml of 2-butanone; 10.4 g of potassium carbonate are then added portionwise, and the mixture is refluxed for one hour. After the addition of 1 g of potassium iodide, there are added dropwise, with stirring and refluxing, 7.1 g of chloroacetonitrile in 30 ml of 2-butanone, and the mixture is subsequently heated for 3 hours at an internal temperature of 75° C. To the resulting reaction mixture, after cooling to room temperature, is added 1 litre of water, and the whole is filtered; the residue is washed with water, dried, and recrystallised from chloroform/petroleum ether (40–60° C.) to thus obtain 2-methyl-5,7-dichloro-8-(cyanomethoxy)-quinoline, m.p. 157–158° C.

Example 2

2-(8-Quinolinoxy)-acetamide oxime (Compound No.2)

A solution of 6.4 g of hydroxylamine hydrochloride in 10 ml of water and 6.4 g of potassium carbonate in 10 ml of water is added dropwise at room temperature, within 15 minutes, to 15.8 g of 8-(cyanomethoxy)-quinoline in 100 ml of ethanol, in the course of which the reaction mixture warms up to 30° C. After 3 hours' stirring at room temperature, the reaction mixture is diluted with 250 ml of water; it is subsequently filtered, and the residue is washed with water and dried. There is thus obtained 2-(8-quinolinoxy)-acetamide oxime in the form of light-brown powder, m.p. 201–204° C. (decomposition).

Example 3

0-(Isopropylaminocarbonyl)-2-(5-chloro-7-bromo-8-quinolinoxy)-acetamide oxime (Compound No. 14).

3.3 g of isopropylisocyanate and 0.1 g of 1,4-diazabicyclo[2,2,2]octane are added at 65° C. with stirring, within 15 minutes, to 8.6 g of 2-(5-chloro-7-bromo-8-quinolinoxy)acetamide oxime in 100 ml of acetonitrile, and the mixture is subsequently heated at 60° C. for two hours. After cooling to room temperature, the reaction mixture is filtered, and the residue is washed with a small amount of acetonitrile and subsequently dried. 0-(Isopropylaminocarbonyl)-2(5-chloro-7-bromo-8-quinolinoxy)-acetamide oxime is thus obtained in the form of white crystals, m.p. 162–165° C.

It is possible to produce, by methods analogous to those described in the foregoing, also the following compounds of the formulae I and Ia, which are listed in Table 1 together with the compounds of the above Examples.

TABLE 1

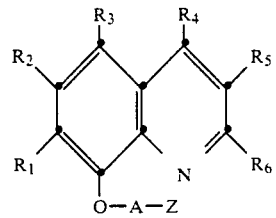

| No. | $R_1$ | $R_2$ | $R_3$ | $R_4$ | $R_5$ | $R_6$ | A | Z | Physical data m.p. |
|---|---|---|---|---|---|---|---|---|---|
| 1 | H | H | H | H | H | H | —CH$_2$— | —CN | 118–119° C. |
| 2 | H | H | H | H | H | H | —CH$_2$— | —C(=NOH)NH$_2$ | 201–204° C. (decomp.) |
| 3 | H | H | H | H | H | CH$_3$ | —CH$_2$— | —CN | 114–116° C. |
| 4 | H | H | H | H | H | CH$_3$ | —CH$_2$— | —C(=NOH)NH$_2$ | 209–210° C. (decomp.) |
| 5 | H | H | Cl | H | H | H | —CH$_2$— | —C(=NOH)NH$_2$ | 203–205° C. (decomp.) |
| 6 | H | H | H | H | H | H | —CH$_2$— | —C(NH$_2$)=N—O—C(=O)NH—C$_3$H$_7$iso | 136–138° C. |
| 7 | H | H | Cl | H | H | H | —CH$_2$— | —CN | 159–160° C. |

TABLE 1-continued

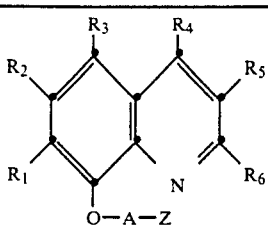

| No. | R₁ | R₂ | R₃ | R₄ | R₅ | R₆ | A | Z | Physical data m.p. |
|---|---|---|---|---|---|---|---|---|---|
| 8 | H | H | H | H | H | H | $-CH_2-$ | $-C(NH_2)=N-O-C(=O)-CH_2Cl$ | 129–130° C. |
| 9 | Br | H | Cl | H | H | H | $-CH_2-$ | $-C(NH_2)=N-OH$ | 197–198° C. (decomp.) |
| 10 | Br | H | Cl | H | H | H | $-CH_2-$ | $-CN$ | 150–151° C. |
| 11 | H | H | H | H | H | H | $-CH_2-$ | $-C(NH_2)=N-O-C(=O)-OCH_3$ | 143–145° C. |
| 12 | J | H | Cl | H | H | H | $-CH_2-$ | $-C(NH_2)=N-OH$ | 195–196° C. (decomp.) |
| 13 | J | H | Cl | H | H | H | $-CH_2-$ | $-CN$ | 141–143° C. |
| 14 | Br | H | Cl | H | H | H | $-CH_2-$ | $-C(NH_2)=N-O-C(=O)-NH-C_3H_7\text{iso}$ | 162–165° C. |
| 15 | Cl | H | Cl | H | H | CH₃ | $-CH_2-$ | $-C(NH_2)=N-OH$ | 205–207° C. (decomp.) |
| 16 | Cl | H | Cl | H | H | H | $-CH_2-$ | $-CN$ | 150–152° C. |
| 17 | J | H | Cl | H | H | H | $-CH_2-$ | $-C(NH_2)=N-O-C(=O)-NH-C_3H_7\text{iso}$ | 163–167° C. |
| 18 | Cl | H | Cl | H | H | CH₃ | $-CH_2-$ | $-CN$ | 157–158° C. |
| 19 | Cl | H | Cl | H | H | CH₃ | $-CH_2-$ | $-C(NH_2)=N-O-C(=O)-NH-C_3H_7\text{iso}$ | 149–152° C. |
| 20 | H | H | H | H | H | H | $-CH_2-CH_2-$ | $-CN$ | 108–112° C. |
| 21 | H | H | H | CH₃ | H | H | $-CH_2-$ | $-CN$ | |

TABLE 1-continued

[Structure: substituted benzene with R1, R2, R3 on one ring; R4, R5, R6 on adjacent positions; with N, O—A—Z group]

| No. | R₁ | R₂ | R₃ | R₄ | R₅ | R₆ | A | Z | Physical data m.p. |
|---|---|---|---|---|---|---|---|---|---|
| 22 | H | H | H | H | H | H | $\underset{-CH-}{CH_3}$ | —CN | 121–124° C. |
| 23 | H | H | CH₃ | H | H | H | —CH₂— | —CN | |
| 24 | H | H | H | H | H | H | —CH₂—CH₂— | $-C\underset{NH_2}{\overset{NOH}{\diagup}}$ | 186–189° C. |
| 25 | H | H | H | H | H | CH₃ | $\underset{-CH-}{CH_3}$ | —CN | |
| 26 | H | H | C₂H₅ | H | H | H | —CH₂— | —CN | |
| 27 | H | H | Br | H | H | H | —CH₂— | $-C\underset{NH_2}{\overset{NOH}{\diagup}}$ | |
| 28 | H | H | H | H | H | CH₃ | —CH₂—CH₂— | —CN | |
| 29 | H | H | H | Br | H | H | —CH₂— | —CN | |
| 30 | H | H | H | H | H | CH₃ | —CH₂—CH₂— | $-C\underset{NH_2}{\overset{NOH}{\diagup}}$ | |
| 31 | H | H | Cl | H | H | H | $\underset{-CH-}{CH_3}$ | —CN | 143–145° C. |
| 32 | H | H | J | H | H | H | —CH₂— | $-C\underset{NH_2}{\overset{NOH}{\diagup}}$ | |
| 33 | H | H | Br | H | H | H | $\underset{-CH-}{CH_3}$ | —CN | |
| 34 | H | H | Br | H | H | CH₃ | —CH₂— | $-C\underset{NH_2}{\overset{NOH}{\diagup}}$ | |
| 35 | H | H | H | H | H | H | $\underset{-CH-}{CH_3}$ | $-C\underset{NH_2}{\overset{NOH}{\diagup}}$ | 191–194° C. (decomp.) |
| 36 | H | H | F | H | H | H | —CH₂— | —CN | |
| 37 | H | H | Cl | H | H | CH₃ | —CH₂— | $-C\underset{NH_2}{\overset{NOH}{\diagup}}$ | |
| 38 | H | H | Br | H | H | CH₃ | $\underset{-CH-}{CH_3}$ | —CN | |

TABLE 1-continued

[Structure: substituted quinoline with R1-R6 substituents and O-A-Z group]

| No. | R₁ | R₂ | R₃ | R₄ | R₅ | R₆ | A | Z | Physical data m.p. |
|---|---|---|---|---|---|---|---|---|---|
| 39 | H | H | H | H | H | CH₃ | -CH(CH₃)- | -C(=NOH)NH₂ | |
| 40 | H | H | Br | H | H | H | -CH₂- | -CN | |
| 41 | Cl | H | Br | H | H | H | -CH₂- | -C(=NOH)NH₂ | |
| 42 | H | H | J | H | H | H | -CH₂- | -CN | |
| 43 | H | H | Cl | H | H | CH₃ | -CH(CH₃)- | -CN | |
| 44 | H | H | Br | H | H | CH₃ | -CH₂- | -CN | |
| 45 | Cl | H | Br | H | H | H | -CH(CH₃)- | -CN | |
| 46 | H | H | Cl | H | H | CH₃ | -CH₂- | -CN | |
| 47 | H | H | Cl | H | H | H | -CH(CH₃)- | -C(=NOH)NH₂ | 186-189° C. (decomp.) |
| 48 | Cl | H | Br | H | H | CH₃ | -CH₂- | -C(=NOH)NH₂ | |
| 49 | H | H | J | H | H | CH₃ | -CH₂- | -CN | |
| 50 | H | H | Br | H | H | H | -CH(CH₃)- | -C(=NOH)NH₂ | |
| 51 | Cl | H | Br | H | H | H | -CH₂- | -CN | |
| 52 | Br | H | Cl | H | H | H | -CH(CH₃)- | -CN | |
| 53 | Br | H | Cl | H | H | CH₃ | -CH₂- | -C(=NOH)NH₂ | |
| 54 | Cl | H | Br | H | H | CH₃ | -CH₂- | -CN | |
| 55 | H | H | Br | H | H | CH₃ | -CH(CH₃)- | -C(=NOH)NH₂ | |
| 56 | Br | H | Cl | H | H | CH₃ | -CH₂- | -CN | |

TABLE 1-continued

[Structure: substituted phenyl-vinyl group with R1, R2, R3 on benzene ring; R4, R5, R6 on vinyl/imine; O-A-Z substituent]

| No. | R₁ | R₂ | R₃ | R₄ | R₅ | R₆ | A | Z | Physical data m.p. |
|-----|----|----|----|----|----|----|----|----|---|
| 57 | J | H | Cl | H | H | H | -CH(CH₃)- | -CN | |
| 58 | J | H | Br | H | H | H | -CH₂- | -CN | |
| 59 | H | H | Cl | H | H | CH₃ | -CH(CH₃)- | -C(=NOH)NH₂ | |
| 60 | Br | H | J | H | H | H | -CH₂- | -CN | |
| 61 | H | H | NO₂ | H | H | H | -CH(CH₃)- | -CN | 154-156° C. |
| 62 | Br | H | NO₂ | H | H | H | -CH₂- | -CN | |
| 63 | J | H | Cl | H | H | CH₃ | -CH₂- | -C(=NOH)NH₂ | |
| 64 | Cl | H | J | H | H | H | -CH₂- | -CN | |
| 65 | Cl | H | NO₂ | H | H | H | -CH₂- | -C(=NOH)NH₂ | 214-216° C. (decomp.) |
| 66 | J | H | Cl | H | H | CH₃ | -CH₂- | -CN | |
| 67 | Br | H | Br | H | H | H | -CH₂- | -C(=NOH)NH₂ | |
| 68 | Cl | H | H | H | H | CH₃ | -CH₂- | -CN | |
| 69 | Cl | H | Br | H | H | H | -CH(CH₃)- | -C(=NOH)NH₂ | |
| 70 | Cl | H | NO₂ | H | H | H | -CH₂- | -CN | 166-169° C. |
| 71 | Cl | H | Cl | H | H | H | -CH₂- | -C(=NOH)NH₂ | |
| 72 | Cl | H | C₃H₇n | H | H | H | -CH₂- | -CN | |
| 73 | Br | H | Br | H | H | H | -CH₂- | -CN | |
| 74 | Br | H | Br | H | H | CH₃ | -CH₂- | -CN | |
| 75 | Br | H | Cl | H | H | H | -CH(CH₃)- | -C(=NOH)NH₂ | |

TABLE 1-continued

[Structure: benzene ring with substituents $R_1$, $R_2$, $R_3$ and $O-A-Z$ group, connected to another ring with $R_4$, $R_5$, $R_6$ and N]

| No. | $R_1$ | $R_2$ | $R_3$ | $R_4$ | $R_5$ | $R_6$ | A | Z | Physical data m.p. |
|---|---|---|---|---|---|---|---|---|---|
| 76 | J | H | J | H | H | H | —CH$_2$— | —C(=NOH)NH$_2$ | |
| 77 | H | H | H | H | H | H | —CH$_2$— | —C(=N—O—C(=O)-cyclopropyl)NH$_2$ | 165–166° C. |
| 78 | J | H | J | H | H | H | —CH$_2$— | —CN | |
| 79 | H | H | H | H | H | H | —CH$_2$— | —C(=N—O—C(=O)—C$_6$H$_4$Cl)NH$_2$ | 139–141° C. |
| 80 | J | H | J | H | H | CH$_3$ | —CH$_2$— | —CN | |
| 81 | H | H | H | H | H | H | —CH$_2$— | —C(=N—O—C(=O)SCH$_3$)NH$_2$ | |
| 82 | NO$_2$ | H | NO$_2$ | H | H | H | —CH$_2$— | —CN | |
| 83 | NO$_2$ | H | NO$_2$ | H | H | CH$_3$ | —CH$_2$— | —C(=NOH)NH$_2$ | |
| 84 | J | H | F | H | H | H | —CH$_2$— | —CN | |
| 85 | H | H | Cl | H | H | H | —CH$_2$— | —C(=N—O—C(=O)CH$_3$)NH$_2$ | 141–143° C. |
| 86 | J | H | NO$_2$ | H | H | CH$_3$ | —CH$_2$— | —CN | |
| 87 | H | H | Cl | H | H | H | —CH$_2$— | —C(=N—O—C(=O)C$_3$H$_7$n)NH$_2$ | |
| 88 | NO$_2$ | H | NO$_2$ | H | H | CH$_3$ | —CH$_2$— | —CN | |

TABLE 1-continued
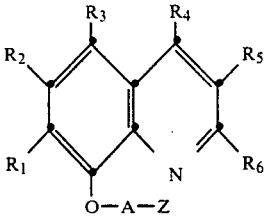
| No. | R₁ | R₂ | R₃ | R₄ | R₅ | R₆ | A | Z | Physical data m.p. |
|---|---|---|---|---|---|---|---|---|---|
| 89 | H | H | Cl | H | H | H | —CH₂— | $-C(NH_2)=N-O-C(=O)-NH-CH_3$ | |
| 90 | H | H | NO₂ | H | H | H | —CH₂— | —CN | 162–164° C. |
| 91 | J | H | Cl | H | H | H | —CH(CH₃)— | $-C(NH_2)=N-OH$ | |
| 92 | H | H | NO₂ | H | H | H | —CH₂— | $-C(NH_2)=N-OH$ | 212–215° C. (decomp.) |
| 93 | H | H | NO₂ | H | H | CH₃ | —CH₂— | —CN | |
| 94 | H | H | Cl | H | H | H | —CH₂— | $-C(NH_2)=N-O-C(=O)-OCH_3$ | 148–149° C. |
| 95 | H | H | H | H | H | CH₃ | —CH₂— | $-C(NH_2)=N-O-C(=O)-NH-CH_3$ | |
| 96 | H | H | NO₂ | H | H | H | —CH(CH₃)— | $-C(NH_2)=N-OH$ | |
| 97 | H | H | H | H | H | CH₃ | —CH₂— | $-C(NH_2)=N-O-C(=O)-CH_3$ | |
| 98 | H | H | Cl | H | H | H | —CH₂— | $-C(NH_2)=N-O-C(=O)-O-C_2H_5$ | 139–140° C. |
| 99 | H | H | H | H | H | H | —CH₂— | $-C(NH_2)=N-O-C(=O)-S-C_5H_{11}n$ | 111–114° C. |

TABLE 1-continued
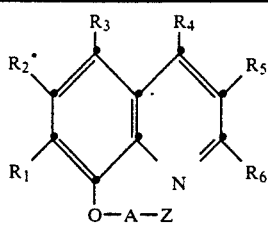
| No. | R₁ | R₂ | R₃ | R₄ | R₅ | R₆ | A | Z | Physical data m.p. |
|---|---|---|---|---|---|---|---|---|---|
| 100 | H | H | H | H | H | H | —CH₂— | $-C(NH_2)=N-O-C(=O)-CHCl-CH_3$ | |
| 101 | H | H | H | H | H | H | —CH₂— | $-C(NH_2)=N-O-C(=O)-CH=CH-CH_3$ | 158–162° C. |
| 102 | H | H | H | H | H | H | —CH₂— | $-C(NH_2)=N-O-C(=O)-NH-C_2H_5$ | 123–125° C. |
| 103 | H | H | H | H | H | H | —CH₂— | $-C(NH_2)=N-O-C(=O)-N(CH_3)(OCH_3)$ | 138–139° C. |
| 104 | H | H | H | H | H | H | —CH₂— | $-C(NH_2)=N-O-C(=O)-C_4H_9n$ | 120–122° C. |
| 105 | H | H | Cl | H | H | H | —CH₂— | $-C(NH_2)=N-O-C(=O)-C_2H_5$ | 157–158° C. (decomp.) |
| 106 | H | H | H | H | H | H | —CH₂— | $-C(NH_2)=N-O-C(=O)-(2,4-Cl_2C_6H_3)$ | |
| 107 | H | H | Cl | H | H | H | —CH₂— | $-C(NH_2)=N-O-C(=O)-O-C_3H_7n$ | |

TABLE 1-continued

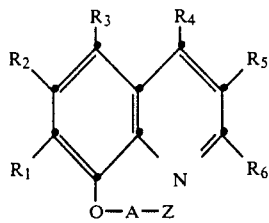

| No. | R₁ | R₂ | R₃ | R₄ | R₅ | R₆ | A | Z | Physical data m.p. |
|---|---|---|---|---|---|---|---|---|---|
| 108 | H | H | H | H | H | H | —CH₂— | $-\underset{NH_2}{C}=N-O-\underset{O}{C}(=O)-CH_2CH_2CH_2Cl$ | 144–146° C. |
| 109 | H | H | Cl | H | H | H | —CH₂— | $-\underset{NH_2}{C}=N-O-\underset{O}{C}(=O)-CH_2-O-CH_3$ | |
| 110 | H | H | H | H | H | H | —CH₂— | $-\underset{NH_2}{C}=N-O-\underset{O}{C}(=O)-CHCl-CH_2Cl$ | 112–114° C. |
| 111 | H | H | Cl | H | H | H | —CH₂— | $-\underset{NH_2}{C}=N-O-\underset{O}{C}(=O)-C_3H_7\text{iso}$ | 173–174° C. |
| 112 | H | H | H | H | H | H | —CH₂— | $-\underset{NH_2}{C}=N-O-\underset{O}{C}(=O)-S-C_4H_9\text{iso}$ | |
| 113 | H | H | Cl | H | H | H | —CH₂— | $-\underset{NH_2}{C}=N-O-\underset{O}{C}(=O)-\text{C}_6\text{H}_4\text{-CH}_3$ | |
| 114 | H | H | H | H | H | H | —CH₂— | $-\underset{NH_2}{C}=N-O-\underset{O}{C}(=O)-O-\text{C}_6\text{H}_5$ | 155–156° C. |

TABLE 1-continued
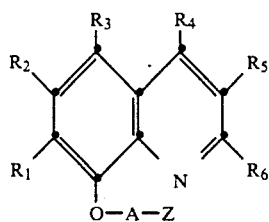
| No. | R₁ | R₂ | R₃ | R₄ | R₅ | R₆ | A | Z | Physical data m.p. |
|---|---|---|---|---|---|---|---|---|---|
| 115 | H | H | H | H | H | H | —CH₂— | −C(=N−O−CO−C₅H₁₁n)(NH₂) | |
| 116 | H | H | H | H | H | H | —CH₂— | −C(=N−O−CO−C₄H₉tert.)(NH₂) | 107–110,5° C. |
| 117 | H | H | H | H | H | H | —CH₂— | −C(=N−O−CO−C₄H₉iso)(NH₂) | 124–126° C. |
| 118 | H | H | H | H | H | H | —CH₂— | −C(=N−O−CO−(2-Cl-C₆H₄))(NH₂) | 131–132° C. |
| 119 | H | H | Cl | H | H | H | —CH₂— | −C(=N−O−CO−(4-Cl-C₆H₄))(NH₂) | |
| 120 | H | H | H | H | H | H | —CH₂— | −C(=N−O−CO−C₆H₁₁)(NH₂) | |

TABLE 1-continued

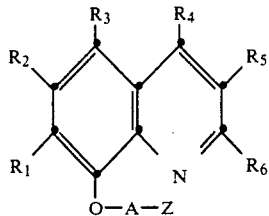

| No. | R₁ | R₂ | R₃ | R₄ | R₅ | R₆ | A | Z | Physical data m.p. |
|-----|----|----|----|----|----|----|---|---|--------------------|
| 121 | H | H | H | H | H | H | —CH₂— | (amidino-oxycarbonyl-NH-4-chlorophenyl) | |
| 122 | H | H | H | H | H | H | —CH₂— | (amidino-oxycarbonyl-CH₂-O-C₄H₉sek.) | 84–86° C. |
| 123 | H | H | H | H | H | H | —CH₂— | (amidino-oxycarbonyl-furyl) | 168–169° C. |
| 124 | H | H | H | H | H | H | —CH₂— | (amidino-oxycarbonyl-CH₂-O-C₄H₇n) | 100–103° C. |
| 125 | H | H | H | H | H | H | —CH₂— | (amidino-oxycarbonyl-4-nitrophenyl) | |
| 126 | H | H | Cl | H | H | H | —CH₂— | (amidino-oxycarbonyl-CH=CH₂) | |
| 127 | H | H | Cl | H | H | H | —CH₂— | (amidino-oxycarbonyl-tetrahydrofuryl) | 156–157° C. (decomp.) |

TABLE 1-continued

[Structure: substituted benzene ring with R1, R2, R3 substituents; attached =CR4-C(R5)=N-R6 group with O-A-Z substituent]

| No. | R1 | R2 | R3 | R4 | R5 | R6 | A | Z | Physical data m.p. |
|-----|----|----|----|----|----|----|----|---|---|
| 128 | H | H | H | H | H | H | —CH2— | -C(NH2)=N-O-C(=O)-C3H7n | 82–85° C. |
| 129 | H | H | H | H | H | H | —CH2— | -C(NH2)=N-O-C(=O)-O-C3H7n | 144–147° C. |
| 130 | H | H | H | H | H | H | —CH2— | -C(NH2)=N-O-C(=O)-NH-C3H7n | |
| 131 | H | H | H | H | H | H | —CH2— | -C(NH2)=N-O-C(=O)-C(CH3)=CH2 | 128–130° C. |
| 132 | H | H | H | H | H | H | —CH2— | -C(NH2)=N-O-C(=O)-N(morpholino) | |
| 133 | H | H | H | H | H | H | —CH2— | -C(NH2)=N-O-C(=O)-O-CH2-CH2Cl | |
| 134 | H | H | H | H | H | H | —CH2— | -C(NH2)=N-O-C(=O)-NH-C4H9n | 90–92° C. |
| 135 | H | H | Cl | H | H | H | —CH2— | -C(NH2)=N-O-C(=O)-CH=CH-CH3 | |

TABLE 1-continued

[Structure: substituted quinoline with R1-R6 substituents and O-A-Z group]

| No. | R1 | R2 | R3 | R4 | R5 | R6 | A | Z | Physical data m.p. |
|-----|----|----|----|----|----|----|----|----|---|
| 136 | H | H | Cl | H | H | H | —CH$_2$— | —C(NH$_2$)=N—O—C(O)—C$_4$H$_9$tert. | |
| 137 | H | H | H | H | H | H | —CH$_2$— | —C(NH$_2$)=N—O—C(O)—CH$_2$Br | 132–134° C. |
| 138 | H | H | H | H | H | H | —CH$_2$— | —C(NH$_2$)=N—O—C(O)—CH(CH$_2$CH$_3$)(CH$_2$CH$_3$) | |
| 139 | H | H | H | H | H | H | —CH$_2$— | —C(NH$_2$)=N—O—C(O)—CH=CH$_2$ (with CH) | 138–140° C. |
| 140 | H | H | H | H | H | H | —CH$_2$— | —C(NH$_2$)=N—O—C(O)—(tetrahydrofuryl) | 129–131° C. |
| 141 | H | H | H | H | H | H | —CH$_2$— | —C(NH$_2$)=N—O—C(O)—O—CH=CH$_2$ | |
| 142 | H | H | H | H | H | H | —CH$_2$— | —C(NH$_2$)=N—O—C(O)—O—C$_4$H$_9$n | 121–123° C. |
| 143 | H | H | H | H | H | H | —CH$_2$— | —C(NH$_2$)=N—O—C(O)—O—CH$_2$—CH=CH$_2$ | 123–125° C. |
| 144 | H | H | Cl | H | H | H | —CH$_2$— | —C(NH$_2$)=N—O—C(O)—C(CH$_3$)=CH$_2$ | |

TABLE 1-continued
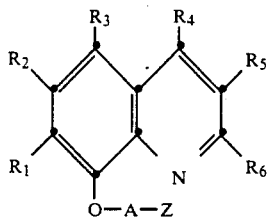
| No. | $R_1$ | $R_2$ | $R_3$ | $R_4$ | $R_5$ | $R_6$ | A | Z | Physical data m.p. |
|---|---|---|---|---|---|---|---|---|---|
| 145 | H | H | H | H | H | H | $-CH_2-$ | {width=0} N-O-C(=O)-S-C₇H₁₅n, with -C(NH₂)= | |
| 146 | H | H | H | H | H | H | $-CH_2-$ | N-O-C(=O)-NH-CH₂-CH₂Cl, with -C(NH₂)= | |
| 147 | H | H | H | H | H | H | $-CH_2-$ | N-O-C(=O)-O-CH₂-CH₂Br, with -C(NH₂)= | 127–128° C. (decomp.) |
| 148 | H | H | H | H | H | H | $-CH_2-$ | N-O-C(=O)-NH-(4-OCH₃-C₆H₄), with -C(NH₂)= | |
| 149 | H | H | Cl | H | H | H | $-CH_2-$ | N-O-C(=O)-cyclopropyl, with -C(NH₂)= | 173–175° C. |
| 150 | H | H | H | H | H | H | $-CH_2-$ | N-O-C(=O)-NH-(3-Cl-C₆H₄), with -C(NH₂)= | |

TABLE 1-continued
| No. | R₁ | R₂ | R₃ | R₄ | R₅ | R₆ | A | Z | Physical data m.p. |
|---|---|---|---|---|---|---|---|---|---|
| 151 | H | H | H | H | H | H | —CH₂— | 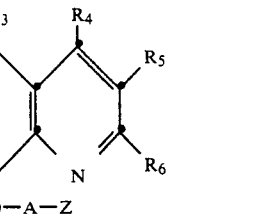 | 135–137° C. |
| 152 | H | H | Cl | H | H | H | —CH₂— | 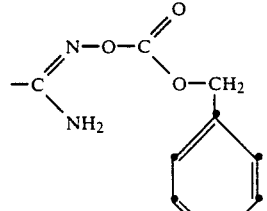 | 191–192° C. (decomp.) |
| 153 | H | H | H | H | H | H | —CH₂— | 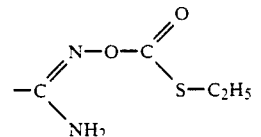 | 120–121° C. |
| 154 | H | H | H | H | H | H | —CH₂— | 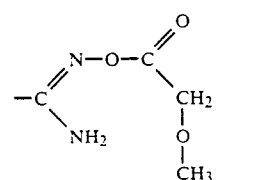 | 118–120° C. |
| 155 | H | H | Cl | H | H | H | —CH₂— | 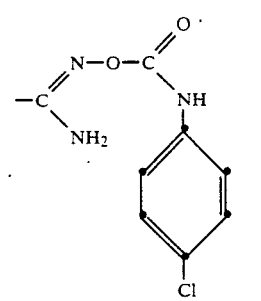 | 191–192° C. (decomp.) |
| 156 | H | H | H | H | H | H | —CH₂— | 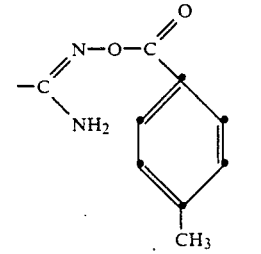 |  |

TABLE 1-continued
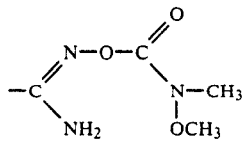
| No. | R₁ | R₂ | R₃ | R₄ | R₅ | R₆ | A | Z | Physical data m.p. |
|-----|----|----|----|----|----|----|---|---|---|
| 157 | H | H | Cl | H | H | H | —CH₂— | 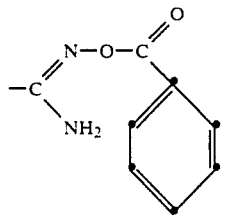 | |
| 158 | H | H | H | H | H | H | —CH₂— | 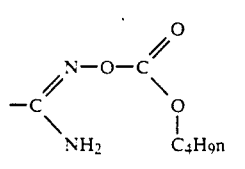 | 158–159° C. |
| 159 | H | H | Cl | H | H | H | —CH₂— | 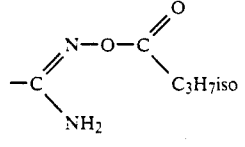 | |
| 160 | H | H | H | H | H | H | —CH₂— | 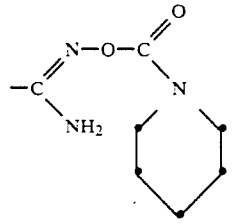 | 115–117.5° C. |
| 161 | H | H | H | H | H | H | —CH₂— | 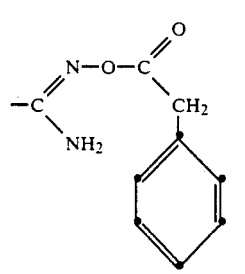 | |
| 162 | H | H | H | H | H | H | —CH₂— | 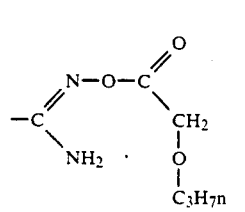 | 140–142° C. |
| 163 | H | H | Cl | H | H | H | —CH₂— | (structure: —C(NH₂)=N—O—C(=O)—CH₂—O—C₃H₇n) | |

TABLE 1-continued
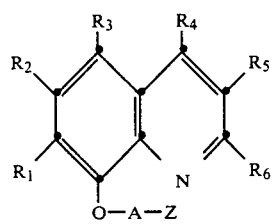
| No. | R₁ | R₂ | R₃ | R₄ | R₅ | R₆ | A | Z | Physical data m.p. |
|-----|----|----|----|----|----|----|----|----|----|
| 164 | H | H | H | H | H | H | —CH₂— | ![structure with p-nitrobenzyl] | |
| 165 | H | H | H | H | H | H | —CH₂— | ![structure with p-nitrophenoxy] | |
| 166 | H | H | H | H | H | H | —CH₂— | ![structure with thiophene] | 164–165° C. |
| 167 | H | H | H | H | H | H | —CH₂— | ![structure with O—C₃H₇iso] | |
| 168 | H | H | Cl | H | H | H | —CH₂— | ![structure with N(CH₃)₂] | |
| 169 | H | H | H | H | H | H | —CH₂— | ![structure with O—C₂H₅] | 129–132° C. |

TABLE 1-continued

[Structure: benzene ring with substituents R1, R2, R3, R4, R5, R6, and O—A—Z group, with N]

| No. | R₁ | R₂ | R₃ | R₄ | R₅ | R₆ | A | Z | Physical data m.p. |
|---|---|---|---|---|---|---|---|---|---|
| 170 | H | H | H | H | H | H | —CH₂— | [structure: =N—O—C(=O)—NH—phenyl, with —C(NH₂)=] | 155–157,5° C. |
| 171 | H | H | H | H | H | H | —CH₂— | [structure: =N—O—C(=O)—O—CH₂—(4-nitrophenyl), with —C(NH₂)=] | |
| 172 | H | H | H | H | H | H | —CH₂— | [structure: =N—O—C(=O)—(3,4-dimethylphenyl), with —C(NH₂)=] | |
| 173 | H | H | Cl | H | H | H | —CH₂— | [structure: =N—O—C(=O)—S—C₂H₅, with —C(NH₂)=] | |
| 174 | H | H | H | H | H | H | —CH₂— | [structure: =N—O—C(=O)—NH—(3-CF₃-phenyl), with —C(NH₂)=] | 158–160° C. |
| 175 | H | H | H | H | H | H | —CH₂— | [structure: =N—O—C(=O)—O—CH₂—C≡CH, with —C(NH₂)=] | |

TABLE 1-continued

| No. | R₁ | R₂ | R₃ | R₄ | R₅ | R₆ | A | Z | Physical data m.p. |
|---|---|---|---|---|---|---|---|---|---|
| 176 | H | H | Cl | H | H | H | —CH₂— | -C(NH₂)=N-O-C(=O)-S-C₃H₇iso | |
| 177 | H | H | Cl | H | H | H | —CH₂— | -C(NH₂)=N-O-C(=O)-CH₂Cl | 155-158° C. (decomp.) |
| 178 | H | H | H | H | H | H | —CH₂— | -C(NH₂)=N-O-C(=O)-CHCl₂ | |
| 179 | H | H | H | H | H | H | —CH₂— | -C(NH₂)=N-O-C(=O)-C₂H₅ | 144-146° C. |
| 180 | H | H | H | H | H | H | —CH₂— | -C(NH₂)=N-O-C(=O)-NH-C₄H₉tert. | |
| 181 | H | H | H | H | H | H | —CH₂— | -C(NH₂)=N-O-C(=O)-CCl₃ | |
| 182 | H | H | H | H | H | H | —CH₂— | -C(NH₂)=N-O-C(=O)-S-C₃H₇iso | 123-124° C. |
| 183 | H | H | H | H | H | H | —CH₂— | -C(NH₂)=N-O-C(=O)-CH₂-CH₂Br | |

TABLE 1-continued
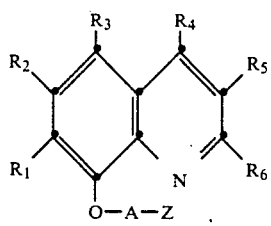
| No. | R₁ | R₂ | R₃ | R₄ | R₅ | R₆ | A | Z | Physical data m.p. |
|---|---|---|---|---|---|---|---|---|---|
| 184 | H | H | H | H | H | H | —CH₂— | (C(NH₂)=N—O—C(=O)—NH—(3,4-dichlorophenyl)) | |
| 185 | H | H | H | H | H | H | —CH₂— | (C(NH₂)=N—O—C(=O)—S—C₃H₇n) | |
| 186 | H | H | H | H | H | H | —CH₂— | (C(NH₂)=N—O—C(=O)—(3,6-dichloropyridazin-4-yl)) | 173–176° C. (decomp.) |
| 187 | H | H | H | H | H | H | —CH₂— | (C(NH₂)=N—O—C(=O)—CH₂—(4-chlorophenyl)) | |
| 188 | H | H | H | H | H | H | —CH₂— | (C(NH₂)=N—O—C(=O)—CH₂—CH₂Cl) | 134–136° C. (decomp.) |
| 189 | H | H | H | H | H | H | —CH₂— | (C(NH₂)=N—O—C(=O)—CH₃) | 100–102° C. |

TABLE 1-continued

[Structure: benzene ring with substituents R1, R2, R3, and CH3, connected via O-A-Z, with a =N-C(R6)=C(R5)-C(R4)= side chain]

| No. | R₁ | R₂ | R₃ | R₄ | R₅ | R₆ | A | Z | Physical data m.p. |
|-----|----|----|----|----|----|----|----|----|--------------------|
| 190 | H | H | H | H | H | H | —CH₂— | [structure: -C(NH₂)=N-O-C(=O)-NH-(4-Cl-3-CF₃-phenyl)] | |
| 191 | H | H | H | H | H | H | —CH₂— | [structure: -C(NH₂)=N-O-C(=O)-NH-CH₃] | |
| 192 | H | H | H | H | H | H | —CH₂— | [structure: -C(NH₂)=N-O-C(=O)-NH-(2,5-dichlorophenyl)] | 197–199° C. |
| 193 | H | H | Cl | H | H | H | —CH₂— | [structure: -C(NH₂)=N-O-C(=O)-phenyl] | |
| 194 | H | H | Cl | H | H | H | —CH₂— | [structure: -C(NH₂)=N-O-C(=O)-NH-C₄H₉tert.] | |
| 195 | H | H | H | H | H | H | —CH₂— | [structure: -C(NH₂)=N-O-C(=O)-(bromofuran with methyl)] | 170–171° C. |

Formulation Examples for liquid active ingredients of the formula I (%=per cent by weight)

| 4. Emulsion concentrates | (a) | (b) | (c) |
|---|---|---|---|
| active ingredient from Table 1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol | — | 12% | 4% |

-continued

| 4. Emulsion concentrates | (a) | (b) | (c) |
|---|---|---|---|
| ether (30 mols of ethylene oxide) | | | |
| cyclohexanone | — | 15% | 20% |
| xylene mixture | 65% | 25% | 20% |

Emulsions of any required concentration can be produced from concentrates of this type by dilution with water.

| 5. Solutions | (a) | (b) | (c) | (d) |
|---|---|---|---|---|
| active ingredient from Table 1 | 80% | 10% | 5% | 95% |
| ethylene glycol-monomethyl ether | 20% | — | — | — |
| polyethylene glycol M G 400 | — | 70% | — | — |
| N-methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 6. Granulates | (a) | (b) |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 7. Dusts | (a) | (b) |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (% = per cent by weight)

| 8. Wettable powders | (a) | (b) | (c) |
|---|---|---|---|
| active ingredient from Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 9. Emulsion concentrate | |
|---|---|
| active ingredient from Table 1 | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |

| 9. Emulsion concentrate | |
|---|---|
| cyclohexanone | 30% |
| xylene mixture | 50% |

Emulsions of the required concentration can be obtained from this concentrate by dilution with water.

| 10. Dusts | (a) | (b) |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| 11. Extruder granulate | |
|---|---|
| active ingredient from Table 1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 12. Coated granulate | |
|---|---|
| active ingredient from Table 1 | 3% |
| polyethylene glycol (M G 200) | 3% |
| kaolin | 94% |

The finely ground active ingredient is evenly applied, in a mixer, to the kaolin moistened with polyethylene glycol. Dustfree coated granules are obtained in this manner.

| 13. Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

Biological Examples

Example 14

Tank mixture in the post-emergence process in the case of barley and wheat

Barley and wheat seeds, respectively, are sown, in a greenhouse, in plastics pots each containing 0.5 litre of soil. After emergence of the plants to the 2- to 3-leaf stage, the substance to be tested as an antidote and also the herbicide 2-[4-(3,5-dichloropyridyl-2-oxy)phenoxy]-propionic acid-2-propinyl ester are applied together as a tank mixture. The protective action of the antidote is estimated in per cent 20 days after application. The plants treated with the herbicide alone and the completely untreated plants provide reference values. The results are summarised in the following Tables: (*AS-=active ingredient)

TABLE 2

Test results for barley

| Antidote compound No. | Antidote kg of AS*/ha | Herbicide kg of AS/ha | Relative protective action in % |
|---|---|---|---|
| 7 | 0,5 | 0,5 | 38 |
| 13 | 0,5 | 0,5 | 25 |

TABLE 3

Test results for wheat

| Antidote compound No. | Antidote kg of AS/ha | Herbicide kg of AS/ha | Relative protective action in % |
|---|---|---|---|
| 1 | 1,5 | 0,75 | 38 |
| 2 | 1,5 | 0,75 | 50 |
| 3 | 1,5 | 0,75 | 50 |
| 4 | 1,5 | 0,75 | 38 |
| 5 | 1,5 | 0,75 | 50 |
| 6 | 1,5 | 0,75 | 50 |
| 7 | 1,5 | 0,75 | 38 |
| 8 | 1,5 | 0,75 | 50 |
| 9 | 1,5 | 0,75 | 25 |
| 10 | 1,5 | 0,75 | 50 |
| 11 | 1,5 | 0,75 | 50 |
| 12 | 1,5 | 0,75 | 50 |
| 13 | 1,5 | 0,75 | 50 |
| 15 | 1,5 | 0,75 | 50 |
| 19 | 1,5 | 0,75 | 38 |

Example 15

Seed swelling with rice; herbicide in the pre-emergence process.

Rice seeds are soaked for 48 hours in solutions of the substance to be tested as antidote at a concentration of 100 ppm, and the seeds are then left to dry for about two hours until they no longer stick together. Plastics containers (length×width×height=25×17×12 cm) are filled to 2 cm below the top edge with sandy loam.

The pre-swelled seeds are sown on the surface of the soil in each container, and only slightly covered with soil, the soil being maintained in a moist (not muddy) state. The herbicide 2-chloro-2',6'-diethyl-N-[2"-(n-propoxy)-ethyl]-acetanilide is then applied as a dilute solution to the surface of the soil. The water level is successively raised to correspond with the growth of the plants. The protective action of the antidote is estimated in per cent 18 days after application of the herbicide. The plants treated with the herbicide alone and the completely untreated plants provide reference values. The results are summarised in the following Table:

TABLE 4

| Antidote compound No. | Antidote ppm | Herbicide kg of AS/ha | Relative protective action in % |
|---|---|---|---|
| 1 | 100 | 0,25 | 50 |
| 8 | 100 | 0,25 | 38 |

Example 16

Tank mixture in the pre-emergence process on soya-bean seeds

Pots (upper diameter 6 cm) are filled with sandy loam, and soya-bean seeds of the "Hark" variety are sown. After the seeds have been covered with soil, the substance to be tested as antidote and the herbicide 4-amino-6-tertbutyl-4,5-dihydro-3-methylthio-1,2,4-triazin-5-one are in dilute solution together sprayed as a tank mixture onto the surface of the soil. The protective action of the antidote is estimated in per cent 21 days after application of the herbicide. The plants treated with the herbicide alone and the completely untreated plants serve as control plants. One result is shown in the following Table:

TABLE 5

| Antidote compound No. | Antidote kg of AS/ha | Herbicide kg of AS/ha | Relative protective action in % |
|---|---|---|---|
| 17 | 1.5 | 0.75 | 38 |

Example 17

Seed dressing with maize: Herbicide in the post-emergence process

Maize seeds of the "LG 5" variety are placed together with the substance to be tested as antidote into a glass container, and well mixed by shaking and rotation. Plastics pots (upper diameter 11 cm) are filled with soil, and the dressed seeds are sown. After the seeds have been covered with soil, the herbicide N-[2-(2-butenyloxy)-phenylsulfonyl]-N'-(4-methoxy-6-methyl-1,3,5-triazin -2-yl)-urea is applied in the post-emergence process. The protective action of the antidote is estimated in per cent 18 days after application of the herbicide. The plants treated with the herbicide alone and the completely untreated plants serve as control plants. The results are summarised in the following Table:

TABLE 6

| Herbicide kg of AS/ha | 1.5 | | | 1.0 | | | 0.5 | | |
|---|---|---|---|---|---|---|---|---|---|
| antidote compound No. 7 g of AS/kg of seed | 4 | 2 | 1 | 4 | 2 | 1 | 4 | 2 | 1 |
| relative protective action in % | 25 | 38 | 38 | 50 | 63 | 50 | 25 | 25 | 25 |

Example 18

Seed dressing with maize: herbicide in the pre-emergence process

Maize seeds of the "LG 5" variety are placed together with the substance to be tested as antidote into a glass container and they are well mixed by shaking and rotation. Plastics pots (upper diameter 11 cm) are filled with soil, and the dressed seeds are sown therein. After the seeds have been covered with soil, the herbicide N-[2-(2-butenyloxy)-phenyl-sulfonyl]-N'-(4-methoxy-6-methyl -1,3,5-triazin-2-yl)-urea is applied in the pre-emergence process. The protective action of the antidote is estimated in per cent 18 days after application of the herbicide. The plants treated with the herbicide alone and the completely untreated plants serve as control plants. One result is given in the following Table:

TABLE 7

| Antidote compound No. | Antidote g of AS/kg of seed | Herbicide kg of AS/ha | Relative protective action in % |
| --- | --- | --- | --- |
| 7 | 1 | 1,0 | 25 |

Example 19

Seed dressing with barley: herbicide in the pre-emergence process

Barley seeds are placed together with the substance to be tested as antidote into a glass container, and the whole is well mixed by shaking and rotation. Plastics containers (length × width × height = 25 × 17 × 12 cm) are filled with sandy loam, and the dressed seeds are sown therein. After the seeds have been covered with soil, the herbicide N-(2-chlorophenylsulfonyl)-N'-(4-methoxy-6-methyl-1,3,5-triazin-2-yl)-urea is sprayed onto the surface of the soil. The protective action of the antidote is estimated in per cent 21 days after application of the herbicide. The plants treated with the herbicide alone and also the completely untreated control plants provide reference values. The results are summarised in the following Table:

TABLE 8

| Antidote compound No. | Antidote g of AS/kg of seed | Herbicide kg of AS/ha | Relative protective action in % |
| --- | --- | --- | --- |
| 7 | 0,5 | 1,0 | 63 |
|  | 0,25 | 1,0 | 63 |
|  | 0,125 | 1,0 | 63 |
| 7 | 0,5 | 0,5 | 75 |
|  | 0,25 | 0,5 | 75 |
|  | 0,125 | 0,5 | 75 |
| 7 | 0,5 | 0,25 | 63 |
|  | 0,25 | 0,25 | 75 |
|  | 0,125 | 0,25 | 63 |
| 7 | 0,5 | 0,125 | 63 |
|  | 0,25 | 0,125 | 63 |
|  | 0,125 | 0,125 | 50 |

Example 20

Seed dressing (wheat): herbicide in the pre-emergence process

Wheat seeds are placed together with the substance to be tested as antidote into a glass container, and the whole is well mixed by shaking and rotation. Plastics containers (length × width × height = 25 × 17 × 12 cm) are filled with sandy loam soil, and the dressed seeds are sown therein. After the seeds have been covered with soil, the herbicide N-(2-chlorophenylsulfonyl)-N'-(4-methoxy-6-methyl-1,3,5-triazin-2-yl)-urea is sprayed onto the surface of the soil. The protective action of the antidote is estimated in per cent 21 days after application of the herbicide. The plants treated with the herbicide alone and also the completely untreated control plants provide reference data. The results are summarised in the following Table:

TABLE 9

| Antidote compound No. | Antidote g of AS/kg of seed | Herbicide kg of AS/ha | Relative protective action in % |
| --- | --- | --- | --- |
| 7 | 1 | 1,5 | 38 |
|  | 0,5 | 1,5 | 38 |
|  | 1 | 1,0 | 25 |
|  | 0,5 | 1,0 | 25 |

Example 21

Seed dressing (barley): herbicide in the post-emergence process

Barley seeds are placed together with the substance to be tested as antidote into a glass container, and the whole is well mixed by shaking and rotation. Plastics containers (length × width × height = 25 × 17 × 12 cm) are filled with sandy loam soil, and the dressed seeds are sown therein. After the seeds have been covered with soil, the herbicide N-(2-chlorophenylsulfonyl)-N'-(4-methoxy-6-methyl-1,3,5-triazin-2-yl)-urea is applied in the post-emergence process. The protective action of the antidote is estimated in per cent 21 days after application. The plants treated with the herbicide alone and also the completely untreated control plants provide reference data. The results are summarised in the following Table:

TABLE 10

| Antidote compound No. | Antidote g of AS/kg of seed | Herbicide kg of AS/ha | Relative protective action in % |
| --- | --- | --- | --- |
| 7 | 2 | 1,5 | 50 |
|  | 1 | 1,5 | 50 |
|  | 0,5 | 1,5 | 63 |
| 7 | 2 | 1,0 | 63 |
|  | 1 | 1,0 | 63 |
|  | 0,5 | 1,0 | 63 |
| 7 | 2 | 0,5 | 38 |
|  | 1 | 0,5 | 38 |
|  | 0,5 | 0,5 | 38 |

Example 22

Seed dressing (wheat): herbicide in the post-emergence process

Wheat seeds are placed together with the substance to be tested as antidote into a glass container, and the whole is well mixed by shaking and rotation. Plastics containers (length × width × height = 25 × 17 × 12 cm) are filled with sandy loam soil, and the dressed seeds are sown therein. After the seeds have been covered with soil, the herbicide N-(2-chlorophenylsulfonyl)-N'-(4-methoxy-6-methyl-1,3,5-triazin-2-yl)-urea is applied in the post-emergence process. The protective action of the antidote is estimated in per cent 21 days after application of the herbicide. The plants treated with herbicide alone and also the completely untreated control plants provide reference values. The results are summarised in the following Table:

TABLE 11

| Antidote compound No. | Antidote g of AS/kg of seed | Herbicide kg of AS/ha | Relative protective action in % |
| --- | --- | --- | --- |
| 7 | 1 | 1,0 | 25 |
|  | 0,5 | 1.0 | 25 |

Example 23

Tank mixture in the post-emergence process on maize

Maize seeds of the "LG 5" variety are sown, in a greenhouse, in plastics pots (upper diameter 11 cm) each containing 0.5 litre of soil. After the seeds have been covered with soil, the substance to be tested as antidote and the herbicide N-[2-(2-butenyloxy)-phenylsulfonyl -N'-(4-methoxy-6-methyl-1,3,5-triazin-2-yl)-urea are applied together as a tank mixture in the post-emergence process. The protective action of the antidote is estimated in per cent 18 days after application. The plants treated with herbicide alone and also the completely untreated control plants provide reference data. One result is shown in the following Table:

TABLE 12

| Antidote compound No. | Antidote kg of AS/ha | Herbicide kg of AS/ha | Relative protective action in % |
|---|---|---|---|
| 7 | 1,0 | 1,0 | 38 |

Example 24

Seed dressing (rice): herbicide in the pre-emergence process

Rice seeds are placed together with the substance to be tested as antidote into a glass container, and the whole is well mixed by shaking and rotation. Containers (length × width × height = 47 × 29 × 24 cm) are filled with sandy loam soil, and the dressed seeds are sown therein. After the seeds have been covered with soil, the herbicide 2-[4-(3,5-dichloropyridyl-2-oxy)-phenoxy]-propionic acid-2-propynyl ester is sprayed as a dilute solution onto the surface of the soil. Twenty days after sowing, when the plants have reached the 3-leaf stage, water is applied until the surface of the soil is covered by a layer of water 4 cm in height. The protective action of the antidote is estimated in per cent 30 days after application of the herbicide. The plants treated with herbicide alone and also the completely untreated plants provide reference data. The results are summarised in the following Table:

TABLE 13

| Antidote compound No. | Antidote g of AS/kg of seed | Herbicide kg of AS/ha | Relative protective action in % |
|---|---|---|---|
| 7 | 0,6 | 0,25 | 50 |
|  | 0,3 | 0,25 | 50 |
|  | 0,2 | 0,25 | 38 |

Example 25

Seed dressing (rice): herbicide in the pre-emergence process

Rice seeds of the IR-36 variety are placed together with the substance to be tested as antidote into a glass container, and the whole is well mixed by shaking and rotation. Plastics containers (length × width × height = 47 × 29 × 24 cm) are filled with sandy loam soil, and the dressed seeds are sown therein. After the seeds have been covered with soil, the herbicide 2-[4-(3,5-dichloropyridyl-2-oxy)-phenoxy]-propionic acid-2-propynyl ester is sprayed onto the surface of the soil. The protective action of the antidote is estimated in per cent 18 days after sowing. The plants treated with herbicide alone and also the completely untreated control plants provide reference data. The results are summarised in the following Table:

TABLE 14

| Antidote compound No. | Antidote g of AS/kg of seed | Herbicide kg of AS/ha | Relative protective action in % |
|---|---|---|---|
| 7 | 0,6 | 0,25 | 50 |
|  | 0,3 | 0,25 | 50 |
|  | 0,2 | 0,25 | 38 |

Example 26

Tank mixture in the post-emergence process on wheat

Wheat seeds of the "Farnese" variety are sown, in a greenhouse, in plastics pots (upper diameter 11 cm) each containing 0.5 litre of soil. After the seeds have been covered with soil, the substance to be tested as antidote and the herbicide 2-chloro-4-trifluoromethylphenyl-3'-oxazolin-2'-yl-4'-nitrophenyl ether are applied together as a tank mixture in the post-emergence process. The protective action of the antidote is estimated in per cent days after application. The plants treated with herbicide alone and the completely untreated control plants provide reference data. The results are summarised in the following Table:

TABLE 15

| Antidote compound No. | Antidote kg of AS/ha | Herbicide kg of AS/ha | Relative protective action in % |
|---|---|---|---|
| 13 | 0,25 | 0,25 | 25 |
|  | 0,125 | 0,25 | 25 |
| 13 | 0,25 | 0,125 | 25 |
|  | 0,125 | 0,125 | 25 |
|  | 0,062 | 0,125 | 25 |

Example 27

Tank mixture in the post-emergence process on wheat

Wheat seeds of the "Farnese" variety are sown, in a greenhouse, in plastics pots (upper diameter 11 cm) each containing 0.5 litre of soil. After the seeds have been covered with soil, the substance being tested as antidote and the herbicide 2-[4-(5-trifluoromethylpyridyl-2-oxy)phenoxy]-propionic acid-n-butyl ester are applied as a tank mixture in the post-emergence process. The protective action of the antidote is estimated in per cent 20 days after application. Plants treated with herbicide alone and completely untreated control plants provide reference data. One result is shown in the following Table:

TABLE 16

| Antidote compound No. | Antidote kg of AS/ha | Herbicide kg of AS/ha | Relative protective action in % |
|---|---|---|---|
| 13 | 0.125 | 0.060 | 25 |

Example 28

Seed dressing (sorghum): herbicide in the pre-emergence process

Sorghum seeds of the "Funk G 623" variety are placed together with the substance to be tested as antidote into a glass container, and the whole is well mixed by shaking and rotation. Plastics pots (upper diameter 11 cm) are filled with soil, and the dressed seed is sown therein. After the seeds have been covered with soil, there is applied as herbicide, in the pre-emergence process, either N-(2-chlorophenylsulfonyl)-N'-(4-methoxy-6-methyl-1,3,5-triazin-2-yl)-urea (A) or N-(2-methoxycarbonylphenylsulfonyl)-N'-4,6-dimethylpyrimidin-2-yl)-urea (B). The protective action of the antidote is estimated in per cent 18 days after application of the herbicide. The plants treated with herbicide alone and also the completely untreated plants provide reference data. The results are summarised in the following Table:

TABLE 17

| Herbicide | | Antidote | | Relative |
| --- | --- | --- | --- | --- |
| Compound | kg of AS/ha | Compound No. | kg of AS/kg of seed | protective action in % |
| A | 0,062 | 7 | 2 | 12,5 |
| | | | 1 | 25 |
| | | | 0,5 | 25 |
| A | 0,031 | 7 | 2 | 25 |
| | | | 1 | 38 |
| | | | 0,5 | 50 |
| A | 0,015 | 7 | 2 | 50 |
| | | | 1 | 63 |
| | | | 0,5 | 63 |
| B | 0,062 | 7 | 2 | 38 |
| | | | 1 | 38 |
| | | | 0,5 | 25 |
| B | 0,031 | 7 | 2 | 50 |
| | | | 1 | 38 |
| | | | 0,5 | 25 |
| B | 0,015 | 7 | 2 | 50 |
| | | | 1 | 50 |
| | | | 0,5 | 50 |

What is claimed is:

1. A process for the protection of cultivated plants against the harmful effects of a herbicide selected from the group consisting of triaziones, chloroacetanilides, pyridyloxyphenoxypropionic acid esters, triazinyl sulfonylureas, pyrimidinyl sulfonylureas and oxazolinyl diphenyl ethers, which process comprises treating the cultivated plants or parts of these plants, or the soil intended for the growing of the cultivated plants, with an antidotally effective amount of a compound of the formula

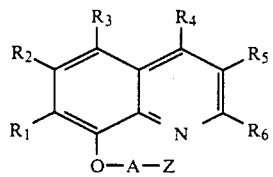

wherein
$R_1$, $R_2$ and $R_3$ independently of one another are each hydrogen, halogen, $C_1$-$C_3$-alkyl, $C_1$-$C_3$-alkoxy, nitro or cyano
R-hd 4, $R_5$ and $R_6$ independently of one another are each hydrogen, halogen or $C_1$-$C_3$-alkyl,
A is any of the groups, —$CH_2$—, —$CH_2$—$CH_2$—, or $CH(CH_3)$—, and
Z is cyano,
including acid addition salts and metal complexes thereof.

2. A process according to claim 1 in which $R_1$ is hydrogen, chlorine, bromine, iodine or nitro; $R_2$ is hydrogen; $R_3$ is hydrogen, fluorine, chlorine, bromine, iodine, $C_1$-$C_3$-alkyl or nitro; $R_4$ is hydrogen, bormine or methyl; $R_5$ is hydrogen; $R_6$ is hydrogen or methyl; and A is —$CH_2$—, —$CH_2$—$CH_2$— or —$CH(CH_3)$—; or a composition comprising an antidotally-effective amount of a compound of the formula as set forth in claim 1 as active ingredient.

3. A process according to claim 2, wherein $R_1$ is hydrogen, chlorine, bromine or iodine; $R_3$ is hydrogen, chlorine or nitro; and $R_4$ and $R_5$ is hydrogen.

4. A process according to claim 3, wherein $R_3$ is hydrogen or chlorine; and A is —$CH_2$—.

5. A process according to claim 4, wherein the compound of the formula is 5-chloro-8-(cyanomethoxy)-quinoline.

6. A process according to claim 4, wherein the compound of the formula is 5-chloro-7-iodo-8-(cyanomethoxy)-quinoline.

7. A process according to claim 1 for the protection of cultivated plants against harmful effects of substituted pyridyloxyphenoxypropionic acid esters.

8. A process according to claim 7 for the protection of cultivated plants against harmful effects of 2-[4-(3,5-dichloropyridyl-2-oxy)-phenoxy]-propionic acid-2-propynyl ester.

9. A process according to claim 1 for the protection of cultivated plants against harmful effects of triazinyl sulfonylureas and pyrimidinyl sulfonylureas.

10. A process according to claim 1 for the protection of rice, maize, wheat, barley, and soya-bean.

11. A composition for the protection of cultivated plants against harmful effects of a herbicide selected from the group consisting of triazines, triazinones, ureas, carbamates, thiocarbamates, chloroacetanilides, chloroacetamide, diphenyl ethers, nitrodiphenyl ethers, benzoic acid derivatives, nitroanilines, oxadiazolenes, phosphates and pyrazoles, which composition comprises (1) a solid agricultural carrier or a liquid agriculturalcarrier plus a surfactant and (2) a compound of the formula

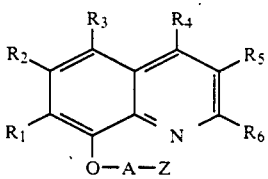

wherein
$R_1$, $R_2$ and $R_3$ independently of one another are each hydrogen, halogen, $C_1$-$C_3$-alkyl, $C_1$-$C_3$-alkoxy, nitro or cyano,
$R_4$, $R_5$ and $R_6$ independently of one another are each hydrogen, halogen or $C_1$-$C_3$-alkyl,
A is any of the groups, —$CH_2$—, —$CH_2$—$CH_2$—$C_2$—, or $CH(CH_3)$—, and
Z is cyano,
including acid addition salts and metal complexes thereof.

12. A composition according to claim 11, wherein
$R_1$ is hydrogen, chlorine, bromine, iodine or nitro,
$R_2$ is hydrogen,
$R_3$ is hydrogen, fluorine, chlorine, bromine, iodine, $C_1$-$C_3$-alkyl or nitro,
$R_4$ is hydrogen, bromine or methyl,
$R_5$ is hydrogen, and
$R_6$ is hydrogen or methyl.

13. A composition according to claim 12, wherein $R_1$ is hydrogen, chlorine, bromine or iodine; $R_3$ is hydrogen, chlorine or nitro; and $R_4$ and $R_5$ is hydrogen.

14. A composition according to claim 13, wherein $R_3$ is hydrogen or chlorine.

15. A composition according to claim 14 which comprises 5-chloro-8-(cyanomethoxy)-quinoline.

16. A composition according to claim 14 which comprises 5-chloro-7-iodo-8-(cyanomethoxy)-quinoline.

17. A composition according to claim 11, which composition comprises a compound of the formula Ia

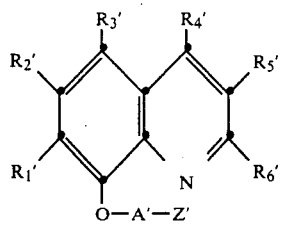

(Ia)

wherein $R'_1$, $R'_2$, and $R'_3$ independently of one another are each hydrogen, halogen, $C_1$-$C_3$-alkyl, $C_1$-$C_3$-alkoxy, nitro or cyano, $R'_4$, $R'_5$, and $R'_6$ independently of one another are each hydrogen, halogen or $C_1$-$C_3$-alkyl, A' is any one of the groups —$CH_2$—, —$CH_2$—$CH_2$— or —$CH(CH_3)$—, and Z' is cyano including acid addition salts and metal complexes thereof, with the proviso that excludes compound wherein simultaneously $R'_1$, $R'_2$, $R'_4$, $R'_5$, and $R'_6$ are hydrogen, $R'_3$ is hydrogen or chlorine, and A' is —$CH_2$— or —$CH(CH_3)$—.

* * * * *